(12) United States Patent
Holoshitz et al.

(10) Patent No.: US 11,168,071 B2
(45) Date of Patent: *Nov. 9, 2021

(54) SMALL MOLECULE INHIBITORS OF SHARED EPITOPE-CALRETICULIN INTERACTIONS AND METHODS OF USE

(71) Applicant: The Regents of the University of Michigan, Ann Arbor, MI (US)

(72) Inventors: Joseph Holoshitz, Ann Arbor, MI (US); Andrew White, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/896,546

(22) Filed: Jun. 9, 2020

(65) Prior Publication Data

US 2020/0299268 A1 Sep. 24, 2020

Related U.S. Application Data

(63) Continuation of application No. 16/183,309, filed on Nov. 7, 2018, now Pat. No. 10,723,718.

(Continued)

(51) Int. Cl.
*A61K 31/454* (2006.01)
*C07D 401/14* (2006.01)
*C07D 405/14* (2006.01)
*A61P 19/00* (2006.01)
*A61K 45/06* (2006.01)
*A61P 37/06* (2006.01)

(52) U.S. Cl.
CPC .......... *C07D 401/14* (2013.01); *A61K 31/454* (2013.01); *A61K 45/06* (2013.01); *A61P 19/00* (2018.01); *A61P 37/06* (2018.01); *C07D 405/14* (2013.01)

(58) Field of Classification Search
CPC .. C07D 401/14; C07D 405/14; A61K 31/454; A61K 45/06; A61P 19/00; A61P 37/06
USPC ........................................................ 514/326
See application file for complete search history.

(56) References Cited

U.S. PATENT DOCUMENTS 6,124,319 A    9/2000  MacCoss et al.
7,074,893 B2   7/2006  Holoshitz et al.
(Continued)

OTHER PUBLICATIONS

Bromley and Woolley, Histopathology of the rheumatoid lesion. Identification of cell types at sites of cartilage erosion. Arthritis Rheum. Aug. 1984;27:857-863.

(Continued)

*Primary Examiner* — Taylor V Oh
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a triazole-methyl-piperidinyl-pyrolyl-propenone structure which function as modulators of shared epitope (SE)—calreticulin (CRT) binding and/or interaction, and their use as therapeutics for the treatment of immuno-regulatory abnormalities (e.g., autoimmune diseases, inflammatory diseases (e.g., chronic inflammatory disease), and bone erosive diseases) by selectively inhibiting SE-CRT interactions and/or signal transduction pathways commonly overactive or dysregulated in arthritic and/or other diseases or conditions.

2 Claims, 10 Drawing Sheets

Related U.S. Application Data

(60) Provisional application No. 62/582,584, filed on Nov. 7, 2017.

(56) References Cited

U.S. PATENT DOCUMENTS

| | | |
|---|---|---|
| 7,208,154 B2 | 4/2007 | Holoshitz et al. |
| 8,586,576 B2 | 11/2013 | Guzi et al. |
| 2005/0250768 A1 | 11/2005 | Link et al. |

OTHER PUBLICATIONS

De Almeida et al., Immune Dysregulation by the Rheumatoid Arthritis Shared Epitope. 2010. The Journal of Immunology 185: 1927-1934.
Fujikawa et al., Bone resorption by tartrate-resistant acid phosphatase-positive multinuclear cells isolated from rheumatoid synovium. Br J Rheumatol. Mar. 1996;35:213-217.
Gonzalez-Gay et al., Influence of human leukocyte antigen-DRB1 on the susceptibility and severity of rheumatoid arthritis. 2002. Semin. Arthritis Rheum. 31: 355-360.
Gravallese et al., Synovial tissue in rheumatoid arthritis is a source of osteoclast differentiation factor. Arthritis Rheum. Feb. 2000;43:250-258.
Gregersen et al., The shared epitope hypothesis. an approach to understanding the molecular genetics of susceptibility to rheumatoid arthritis. Arthritis Rheum. Nov. 1987;30:1205-1213.
Holoshitz et al., A role for calreticulin in the pathogenesis of rheumatoid arthritis. Oct. 2010 Ann. N. Y. Acad. Sci. 1209: 91-98.
Holoshitz et al., An HLA-DRB1-Coded Signal Transduction Ligand Facilitates Inflammatory Arthritis: A New Mechanism of Autoimmunity. Nov. 2012, J. Immunol, 10 pages.
Jawaheer et al., "Homozygosity" for the HLA-DR shared epitope contributes the highest risk for rheumatoid arthritis concordance in identical twins. May 1994 Arthritis Rheum. 37: 681-686.
Kotake et al., IL-17 in synovial fluids from patients with rheumatoid arthritis is a potent stimulator of osteoclastogenesis. May 1999 J. Clin. Invest. 103: 1345-1352.
Ling et al., Activation of nitric oxide signaling by the rheumatoid arthritis shared epitope. Oct. 2006. Arthritis Rheum. 54: 3423-3432.
Ling et al., The rheumatoid arthritis shared epitope increases cellular susceptibility to oxidative stress by antagonizing an adenosine-mediated anti-oxidative pathway. 2007. Arthritis Res Ther 9: R5, pp. 1-12.
Ling et al., The Rheumatoid Arthritis Shared Epitope Triggers Innate Immune Signaling via Cell Surface Calreticulin. Nov. 2007. The Journal of Immunology 179: 6359-6367.
Ling et al. Citrullinated calreticulin potentiates rheumatoid arthritis shared epitope signaling. Mar. 2013;65(3):618-26.
Marotte et al., The association between periodontal disease and joint destruction in rheumatoid arthritis extends the link between the HLA-DR shared epitope and severity of bone destruction. Ann Rheum Dis. 2006 65:905-909.
Mattey et al., Independent association of rheumatoid factor and the HLA-DRB1 shared epitope with radiographic outcome in rheumatoid arthritis. Jul. 2001. Arthritis Rheum. 44: 1529-1533.
Plant et al., Patterns of radiological progression in early rheumatoid arthritis: results of an 8 year prospective study. 1998 J. Rheumatol. 25: 417-426.
Sato et al., Th17 functions as an osteoclastogenic helper T cell subset that links T cell activation and bone destruction. 2006 J. Exp. Med. 203: 2673-2682.
Shahrara et al., TH-17 cells in rheumatoid arthritis. 2008 Arthritis Res Ther 10: R93, pp. 1-7.
Weyand et al., Disease mechanisms in rheumatoid arthriti: Gene dosage effect of HLA-DR haplotypes. 1994. J. Lab. Clin. Med. 124: 335-338.
Wucherpfennig and Strominger, Selective Binding of Self Peptides to Disease-associated Major Histocompatibility Complex (MHC) Molecules: . . . , J Exp Med. May 1, 1995;181:1597-1601.
International Search Report and Written Opinion, International Patent Application No. PCT/US2018/059623, dated Jan. 18, 2019, 9 pages.
Pubchem, Substance Record of SID 277470199. Available Date: Jan. 12, 2016 [retrieved on Dec. 7, 2018] 5 pages.

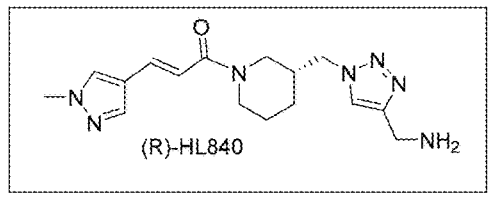

(R)-HL840

(R,E)-1-(3-((4-(aminomethyl)-1H-1,2,3-triazol-1-yl)methyl)piperidin-1-yl)-3-(1-methyl-1H-pyrazol-4-yl)prop-2-en-1-one

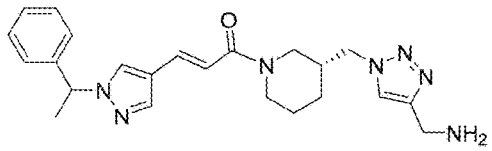

(E)-1-((R)-3-((4-(aminomethyl)-1H-1,2,3-triazol-1-yl)methyl)piperidin-1-yl)-3-(1-(1-phenylethyl)-1H-pyrazol-4-yl)prop-2-en-1-one

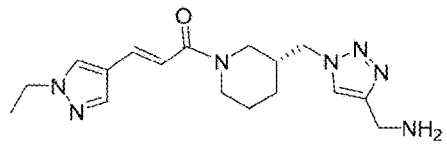

(R,E)-1-(3-((4-(aminomethyl)-1H-1,2,3-triazol-1-yl)methyl)piperidin-1-yl)-3-(1-ethyl-1H-pyrazol-4-yl)prop-2-en-1-one

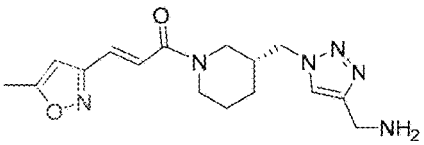

(R,E)-1-(3-((4-(aminomethyl)-1H-1,2,3-triazol-1-yl)methyl)piperidin-1-yl)-3-(5-methylisoxazol-3-yl)prop-2-en-1-one

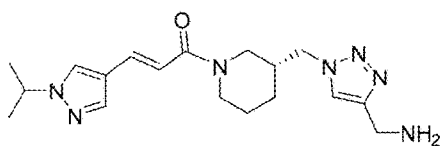

(R,E)-1-(3-((4-(aminomethyl)-1H-1,2,3-triazol-1-yl)methyl)piperidin-1-yl)-3-(1-isopropyl-1H-pyrazol-4-yl)prop-2-en-1-one

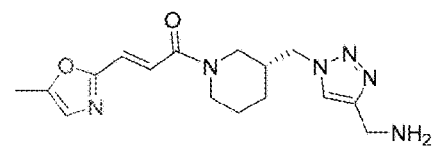

(R,E)-1-(3-((4-(aminomethyl)-1H-1,2,3-triazol-1-yl)methyl)piperidin-1-yl)-3-(5-methyloxazol-2-yl)prop-2-en-1-one

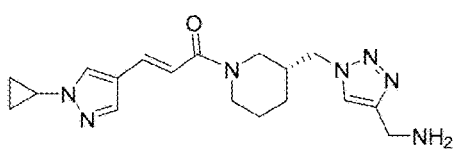

(R,E)-1-(3-((4-(aminomethyl)-1H-1,2,3-triazol-1-yl)methyl)piperidin-1-yl)-3-(1-cyclopropyl-1H-pyrazol-4-yl)prop-2-en-1-one ALL the changes left and above can be combined with below:-

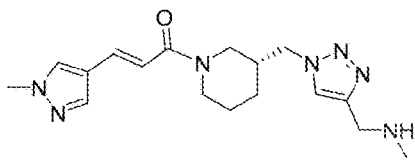

(R,E)-3-(1-methyl-1H-pyrazol-4-yl)-1-(3-((4-((methylamino)methyl)-1H-1,2,3-triazol-1-yl)methyl)piperidin-1-yl)prop-2-en-1-one

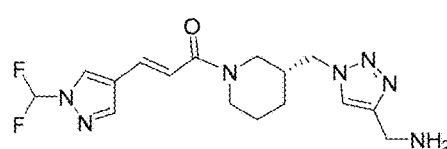

(R,E)-1-(3-((4-(aminomethyl)-1H-1,2,3-triazol-1-yl)methyl)piperidin-1-yl)-3-(1-(difluoromethyl)-1H-pyrazol-4-yl)prop-2-en-1-one

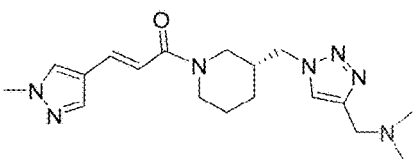

(R,E)-1-(3-((4-((dimethylamino)methyl)-1H-1,2,3-triazol-1-yl)methyl)piperidin-1-yl)-3-(1-methyl-1H-pyrazol-4-yl)prop-2-en-1-one

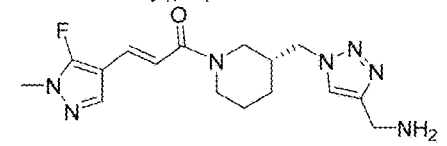

(R,E)-1-(3-((4-(aminomethyl)-1H-1,2,3-triazol-1-yl)methyl)piperidin-1-yl)-3-(5-fluoro-1-methyl-1H-pyrazol-4-yl)prop-2-en-1-one

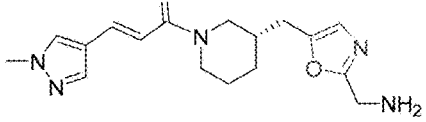

(S,E)-1-(3-((2-(aminomethyl)oxazol-5-yl)methyl)piperidin-1-yl)-3-(1-methyl-1H-pyrazol-4-yl)prop-2-en-1-one FIG. 6
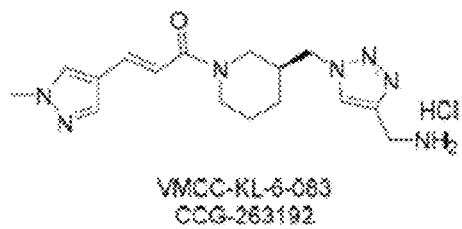 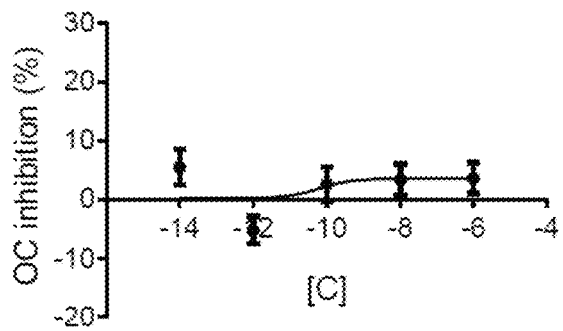
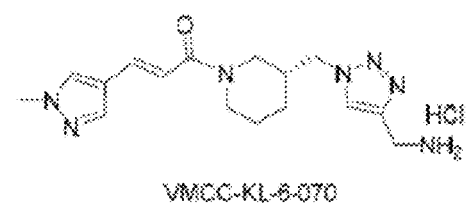 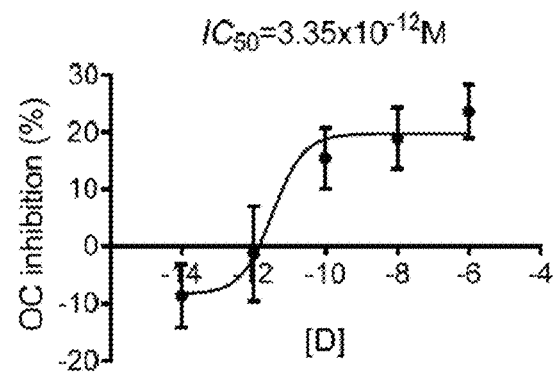
$IC_{50}=3.35\times10^{-12}M$
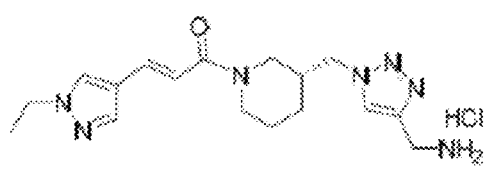 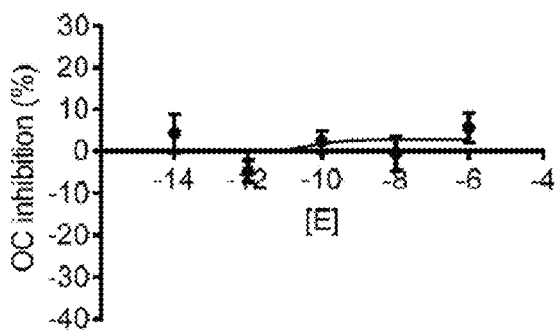
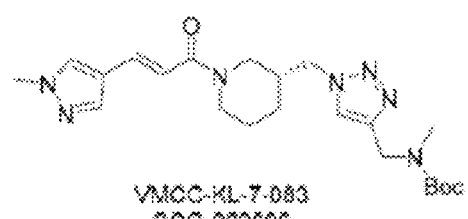 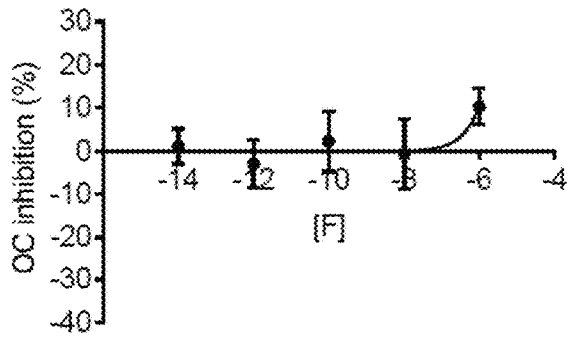

FIG. 6 (CONT'D)
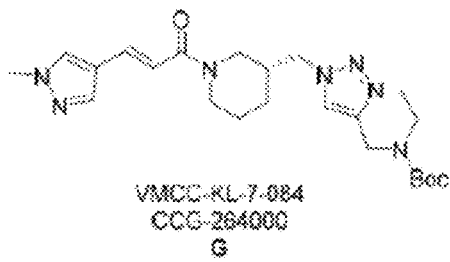
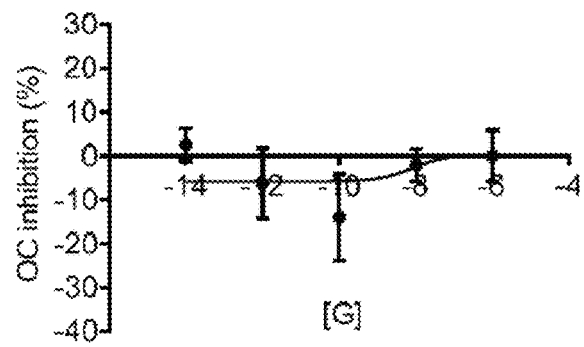
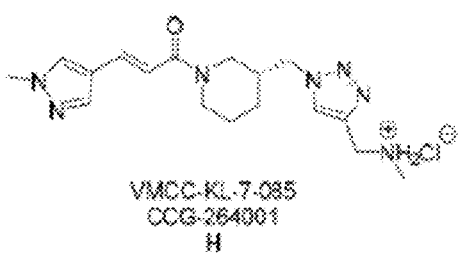
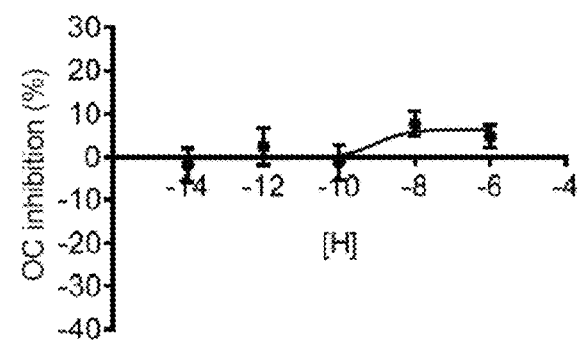
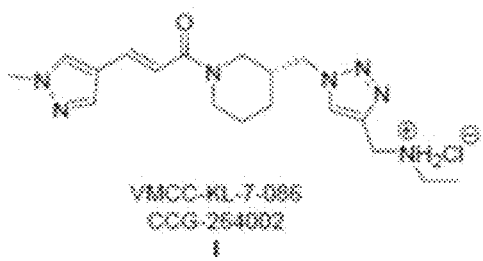
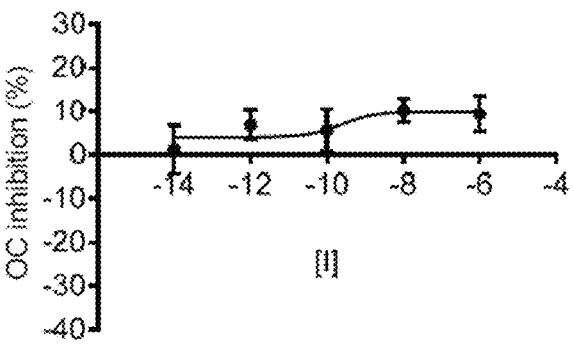
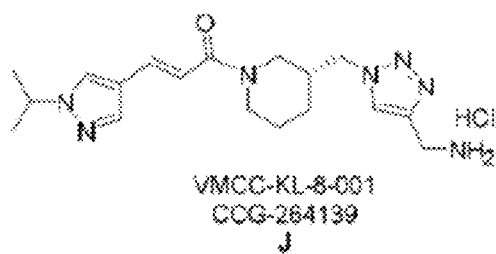
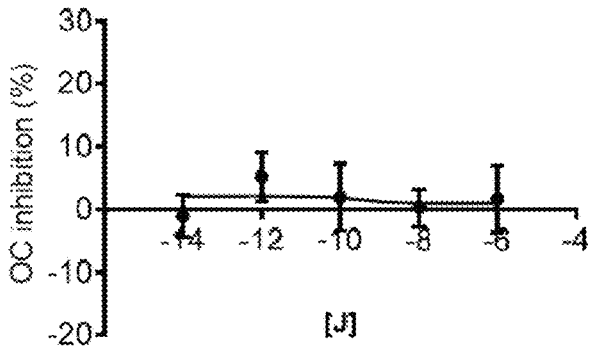

FIG. 6 (CONT'D)
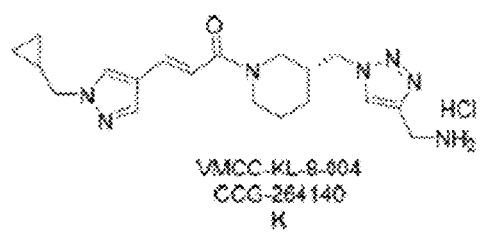
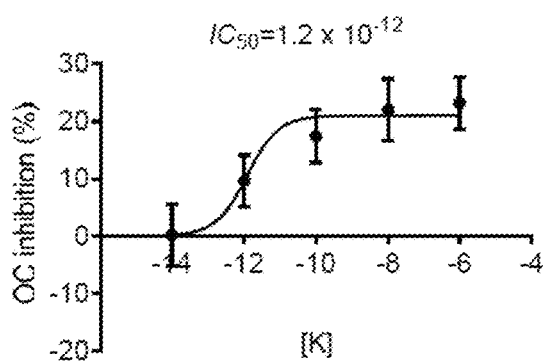
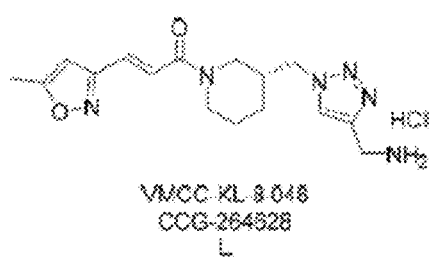
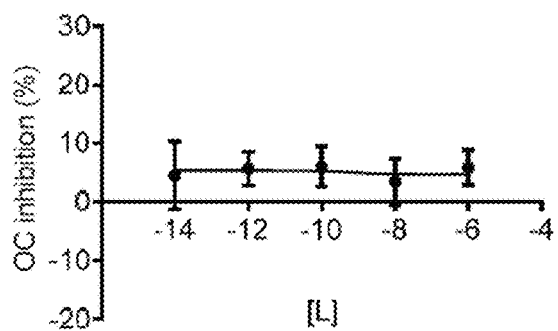

SMALL MOLECULE INHIBITORS OF SHARED EPITOPE-CALRETICULIN INTERACTIONS AND METHODS OF USE

CROSS REFERENCE TO RELATED APPLICATION

This application is a continuation of U.S. patent application Ser. No. 16/183,309, filed Nov. 7, 2018, which claims priority to and the benefit of U.S. Provisional Application No. 62/582,584, filed Nov. 7, 2017, which are hereby incorporated by reference their entireties.

FIELD OF THE INVENTION

This invention is in the field of medicinal chemistry. In particular, the invention relates to a new class of small-molecules having a triazole-methyl-piperidinyl-pyrolyl-propenone structure which function as modulators of shared epitope (SE)—calreticulin (CRT) binding and/or interaction, and their use as therapeutics for the treatment of immuno-regulatory abnormalities (e.g., autoimmune diseases, inflammatory diseases (e.g., chronic inflammatory disease), and bone erosive diseases) by selectively inhibiting SE-CRT interactions and/or signal transduction pathways commonly overactive or dysregulated in arthritic and/or other diseases or conditions.

INTRODUCTION

Rheumatoid arthritis (RA) and periodontal disease are both characterized by chronic inflammation and bone erosions (See, e.g., Bromley and Woolley, Arthritis Rheum. August 1984; 27:857-863, Fujikawa et al., Br J Rheumatol. March 1996; 35:213-217, Gravallese et al., Arthritis Rheum. February 2000; 43:250-258, Marotte et al., Ann Rheum Dis. 2006 65:905-909). Both diseases are associated with HLA-DRB1 alleles coding a five amino acid sequence motif called the 'shared epitope' (SE) in the region 70-74 of the DRβ chain (See, e.g., Gregersen et al., Arthritis Rheum. 1987; 30:1205-1213). In RA, the SE not only confers a higher risk, but also increases the likelihood of developing a more severe disease. In periodontal disease, likewise, SE is associated with more severe bone destruction (See, e.g., Marotte et al., Ann Rheum Dis. 2006 65:905-909).

The underlying mechanisms by which the SE affects susceptibility to and severity of bone damage are unknown. The prevailing hypothesis postulates that the SE allows presentation of putative self or foreign arthritogenic antigens (See, e.g., Wucherpfennig and Strominger, J Exp Med. May 1 1995; 181:1597-1601); however, the identities of such target antigens remain elusive.

RA is a chronic, systemic inflammatory disorder that may affect many tissues and organs, but principally attacks flexible (synovial) joints. It can be a disabling and painful condition which can lead to substantial loss of functioning and mobility if not adequately treated.

The process involves an inflammatory response of the capsule around the joints (synovium) secondary to swelling (hyperplasia) of synovial cells, excess synovial fluid, and the development of fibrous tissue (pannus) in the synovium. The pathology of the disease process often leads to the destruction of articular bone and cartilage, and ankylosis (fusion) of the joints. Rheumatoid arthritis can also produce diffuse inflammation in the lungs, membrane around the heart (pericardium), the membranes of the lung (pleura), and white of the eye (sclera), and also nodular lesions, most common in subcutaneous tissue.

Although the cause of RA is unknown, autoimmunity plays a pivotal role in both its chronicity and progression and RA is considered a systemic autoimmune disease. It is a clinical diagnosis made on the basis of symptoms, physical exam, radiographs (X-rays) and labs.

Preventing bone damage in RA, periodontal disease, and other erosive bone diseases remains a challenge. Most current and emerging drugs are targeted at generic, "downstream" immune pathways or inflammatory cytokines. As a result, drug failure and/or side effects are common. Despite their potency, peptidomimetics may have disadvantages due to their relatively large molecular mass (~1000 Da) thereby compromising bioavailability and complicating chemical optimization and large-scale synthesis.

Improved techniques for treating and/or preventing RA and bone damage related to RA, periodontal disease, and other erosive bone diseases are needed.

The present invention addresses this need.

SUMMARY OF THE INVENTION

Experiments conducted during development of embodiments of the invention identified HL840

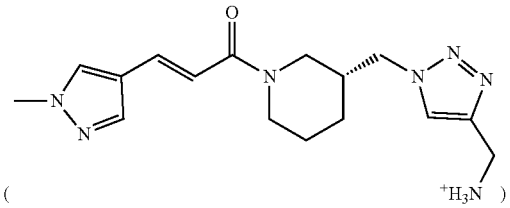 [SMILES: Cn1cc(/C=C/C(=O)N2CCC[C@@H](Cn3cc(C[NH3+])nn3)C2)cn1]

((R,E)-(1-((1-(3-(1-methyl-1H-pyrazol-4-yl)acryloyl)piperidin-3-yl)methyl)-1H-1,2,3-triazol-4-yl)methanaminium) as a moderately orally available, potent anti-OC small molecule that displays strong anti-arthritis and anti-bone erosion effects in vivo when administered orally to mice with pre-clinical models of RA (See, e.g., Examples 1-3).

Further experiments were performed in order to determine if the enantiomers of HL840 displayed different pharmacological properties including potency and metabolic stability. Novel synthesis schemes were generated in order to synthesize the racemate and both enantiomers. As shown in FIG. 3, the (R)-enantiomer was responsible for all activity (e.g., inhibition of SE-CRT interaction and signaling) of racemic HL840.

Further experiments identified additional small molecules having a triazole-methyl-piperidinyl-pyrolyl-propenone structure and structurally similar which function as modulators of shared epitope (SE)—calreticulin (CRT) binding and/or interaction (see, e.g., Example 4 and FIG. 6).

As such, the present invention provides a new class of small-molecules having a triazole-methyl-piperidinyl-pyrolyl-propenone structure which function as modulators of shared epitope (SE)—calreticulin (CRT) binding and/or interaction, and as therapeutics for the treatment of immunoregulatory abnormalities (e.g., autoimmune diseases, inflammatory diseases (e.g., chronic inflammatory disease), and bone erosive diseases) by selectively inhibiting SE-CRT interactions and/or signal transduction pathways commonly overactive or dysregulated in arthritic and/or other diseases or conditions.

Accordingly, the present invention contemplates that exposure of animals (e.g., humans) suffering from immunoregulatory abnormalities (e.g., autoimmune diseases, inflammatory diseases (e.g., chronic inflammatory disease), and bone erosive diseases) to therapeutically effective amounts of drug(s) (e.g., small molecules) having a triazole-methyl-piperidinyl-pyrolyl-propenone structure that selectively inhibit SE-CRT interactions will prevent and/or ameliorate the effects of such immunoregulatory abnormalities.

The present invention contemplates that inhibitors of SE-CRT satisfy an unmet need for the treatment of immunoregulatory abnormalities (e.g., autoimmune diseases, inflammatory diseases (e.g., chronic inflammatory disease), and bone erosive diseases), either when administered as monotherapy, or when administered in a temporal relationship with additional agent(s), such as other pharmaceutical agents known to be effective in treating such conditions or symptoms related to such conditions (combination therapies).

The Applicants have found that certain triazole-methyl-piperidinyl-pyrolyl-propenone compounds function as modulators of SE-CRT binding and/or interaction, and serve as therapeutics for the treatment of immunoregulatory abnormalities (e.g., autoimmune diseases, inflammatory diseases (e.g., chronic inflammatory disease), and bone erosive diseases) and other diseases. Thus, the present invention relates to triazole-methyl-piperidinyl-pyrolyl-propenone compounds useful for inhibiting SE-CRT binding and/or interaction. Certain triazole-methyl-piperidinyl-pyrolyl-propenone compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art. In one example, a formulation scheme shown in FIG. 4 is used to prepare the compound. However, the invention is not so limited. Indeed, one of ordinary skill in the art recognizes variations in the scheme of FIG. 4 which are appropriate for the preparation of the compound of the present invention.

In a particular embodiment, triazole-methyl-piperidinyl-pyrolyl-propenone compounds and structurally similar compounds encompassed within Formulas I, II, III, and IV are provided:

(Formula I)

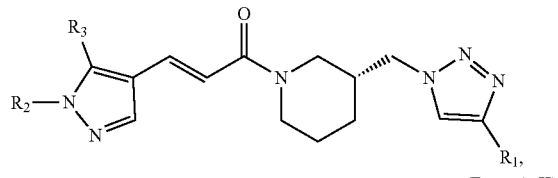

(Formula II)

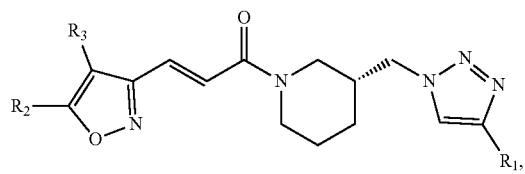

(Formula III)

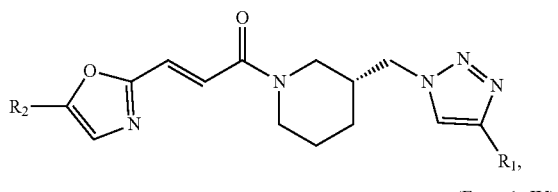

(Formula IV)

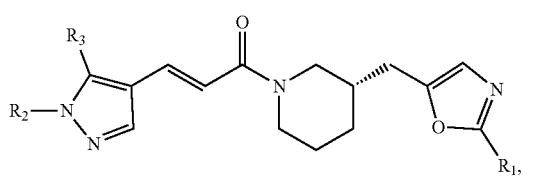

including pharmaceutically acceptable salts, solvates, and/or prodrugs thereof.

Formulas I, II, III and IV are not limited to a particular chemical moiety for R1, R2, and R3. In some embodiments, the particular chemical moiety for R1, R2, and R3 independently include any chemical moiety that permits the resulting compound to modulate of SE-CRT binding and/or interaction.

In some embodiments, R1 is

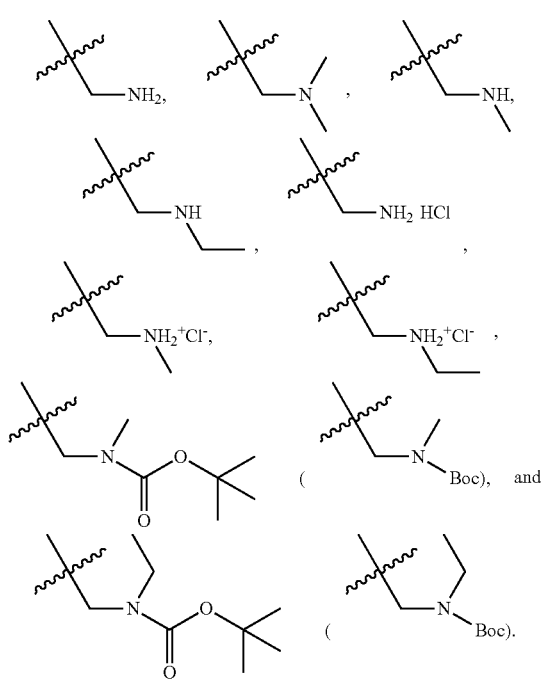

In some embodiments, R2 is $CH_3$,

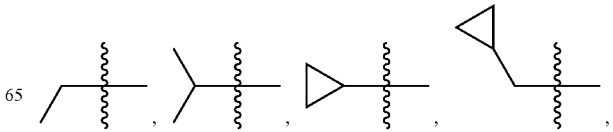

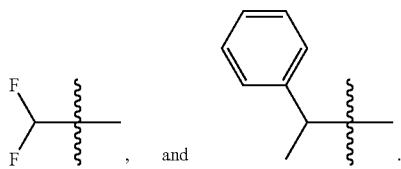, and 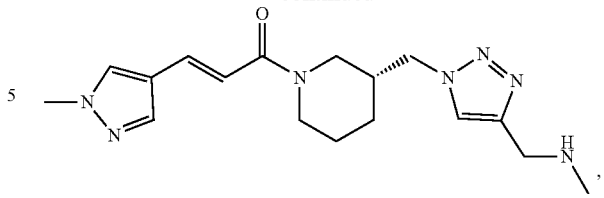.

In some embodiments, R3 is hydrogen or fluorine.

In some embodiments, the following compounds are contemplated for Formulas I, II, III and IV:

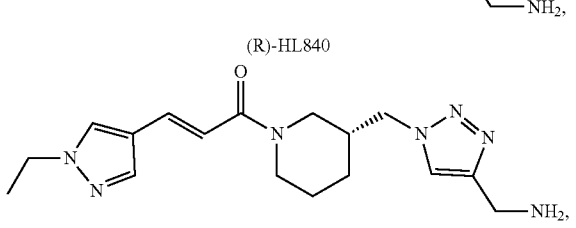

(R)-HL840

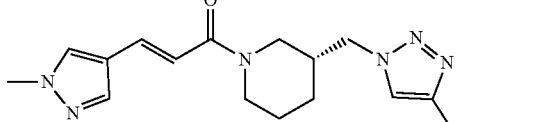

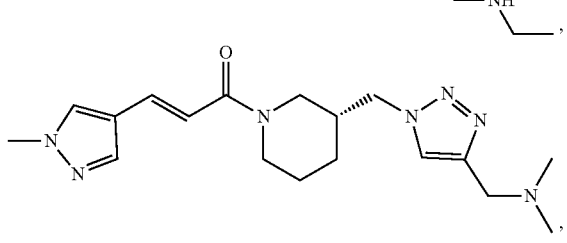

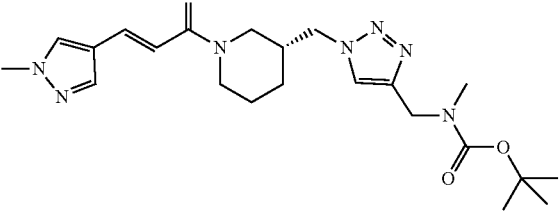

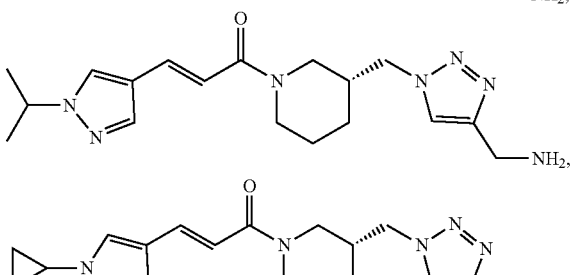

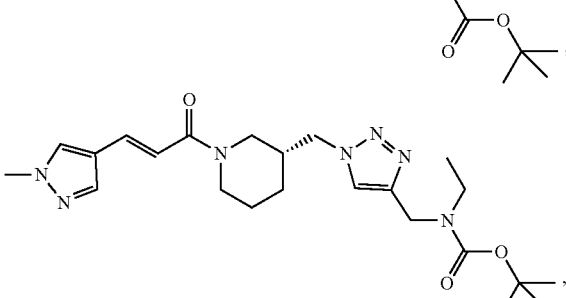

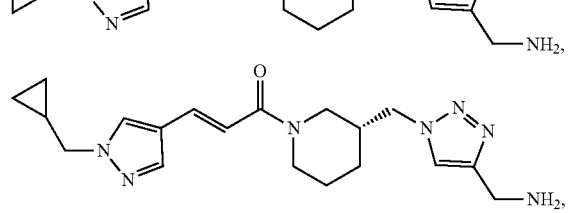

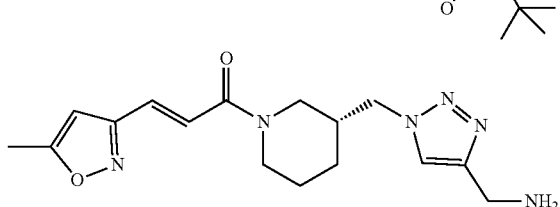

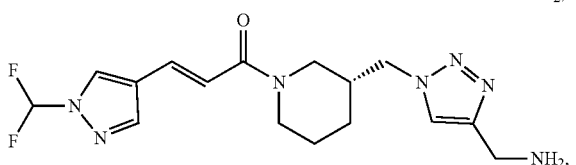

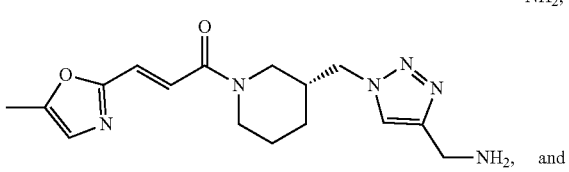, and

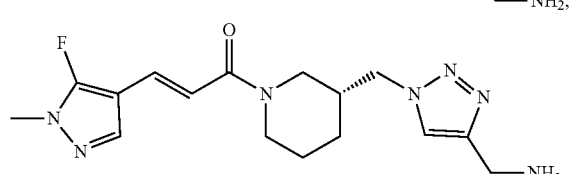

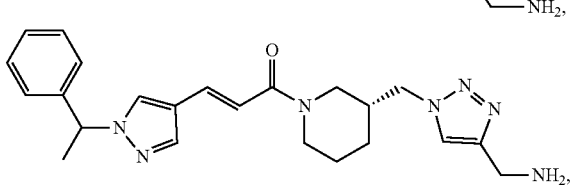

or a pharmaceutically acceptable salt, solvate, or prodrug thereof.

The invention further provides processes for preparing any of the compounds of the present invention through following at least a portion of the techniques recited the Examples. For example, in some embodiments, the present invention provides a process for preparing a compound having the formula:

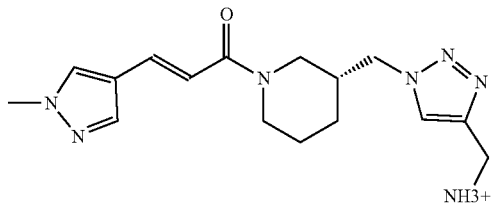 [SMILES: Cn1cc(/C=C/C(=O)N2CCC[C@@H](Cn3cc(C[NH3+])nn3)C2)cn1]

comprising (a) starting with piperidin-3-ylmethanol, N-benzyl protecting and converting the alcohol to the mesylate to prepare a compound having the structure:

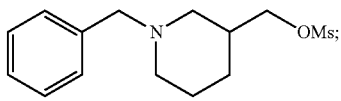 [SMILES: CS(=O)(=O)OCC1CCCN(Cc2ccccc2)C1]

(b) displacing the mesylate with azide to prepare the intermediate:

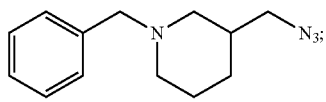 [SMILES: [N-]=[N+]=NCC1CCCN(Cc2ccccc2)C1]

(c) cyclization with substituted alkyne to prepare:

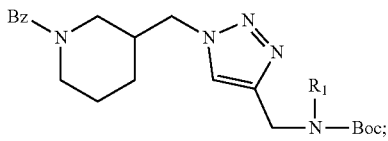

(d) debenzylation to prepare:

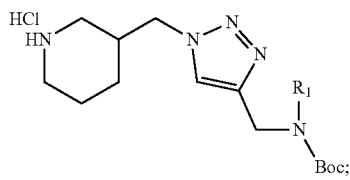

(e) coupling of carboxylic acid analogs to prepare:

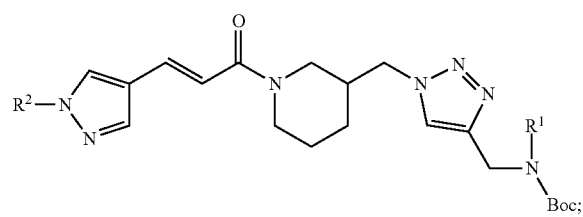

and (f) removing the Boc protecting group to prepare

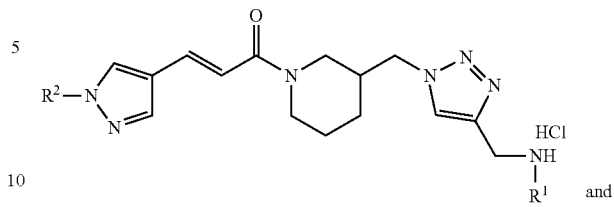

CCG-262662, R2 = Me, R1 = H

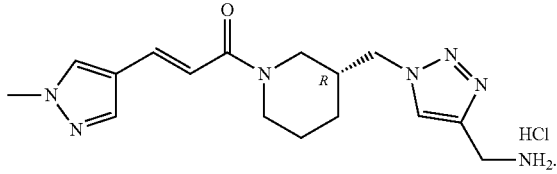

CCG-263109

In another aspect, the invention provides methods of treating an immunoregulatory abnormality in a subject (e.g., a mammalian patient) in need of such treatment comprising administering to the patient a compound of the invention in an amount that is effective for treating the immunoregulatory abnormality. The invention is not limited to any particular immunoregulatory abnormality. In one embodiment, the immunoregulatory abnormality is an autoimmune disease. In another embodiment, the immunoregulatory abnormality is a chronic inflammatory disease. In one embodiment, the autoimmune disease or chronic inflammatory disease is rheumatoid arthritis. In one embodiment, the treatment inhibits and/or reduces bone erosion in the subject. Other immunoregulatory abnormalities may be treated including, but not limited to transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C.sub.4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/ non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

In yet another embodiment, the invention provides methods of suppressing the immune system in a subject (e.g., mammalian patient) in need of immunosuppression comprising administering to the patient an immunosuppressing effective amount of a compound of the invention. In a further embodiment, a compound of the invention is combined with a pharmaceutically acceptable carrier (e.g., to generate a pharmaceutical composition). Compounds of the invention, and pharmaceutical compositions comprising same, find use in methods of treating a disease or condition characterized with bone erosion and/or bone loss in a subject (e.g., a mammalian patient) comprising administering to the subject (e.g., patient) a composition (e.g., a pharmaceutical composition) of the invention in an amount that is effective for treating the bone erosion and/or bone loss disease or condition. The invention is not limited by the type of bone loss disease or condition treated. Indeed, a variety of bone loss diseases or conditions may be treated including, but not limited to, rheumatoid arthritis, a bone destroying arthritic condition, periodontal disease, osteoporosis, osteomyelitis, bone metastasis, bone fracture healing, or other disease or condition in which bone loss and/or bone erosion is present.

In yet another embodiment, compositions and methods of the invention can be used in methods of treatment of a subject (e.g., a mammalian patient) to enhance and/or maintain bone density, bone mass, and/or bone structure.

In another embodiment, the invention provides a therapeutically effective amount of a compound of the present invention, and the physiologically acceptable salts, derivatives, prodrugs, and solvates thereof, including mixtures thereof in all ratios, for use in treating or delaying the progression of an immunoregulatory abnormality in a subject (e.g., mammalian patient) in need of such treatment. In one embodiment, the compound displays desirable permeability characteristics (e.g., for oral delivery). In one embodiment, the composition for use in treating or delaying the progression of an immunoregulatory abnormality further comprises one or more anti-inflammatory and/or anti-rheumatic compositions. The invention is not limited by the type of anti-inflammatory and/or anti-rheumatic composition. Indeed, any anti-inflammatory and/or anti-rheumatic composition known to those of ordinary skill in the art may be used in combination with a compound of the invention. In one embodiment, the immunoregulatory abnormality is a bone destroying disease or condition (e.g., rheumatoid arthritis). In one embodiment, the treating reduces or eliminates bone erosion and/or bone loss. In another embodiment, the treating enhances and/or maintains bone density, bone mass, and/or bone structure.

The invention also provides kits comprising a medicament comprising a compound of the invention (e.g., independently or in combination with a pharmaceutically acceptable carrier), and a package insert comprising instructions for administration of the medicament for treating or delaying progression of bone erosion and/or bone loss in a mammalian patient. The kits may optionally contain other therapeutic agents, e.g., anti-inflammatory agents and/or anti-rheumatic agents.

BRIEF DESCRIPTION OF DRAWINGS

FIG. 5 shows (R)-HL840 and related analogs.

FIG. 6 shows various graphs depicting the biologic activities of HL840 and structurally similar compounds. Specifically, FIG. 6 shows RAW 264.7 cells cultured in osteoclast (OC)-differentiating conditions in the presence or absence of various, and IC50 values.

DEFINITIONS

Figure 1:
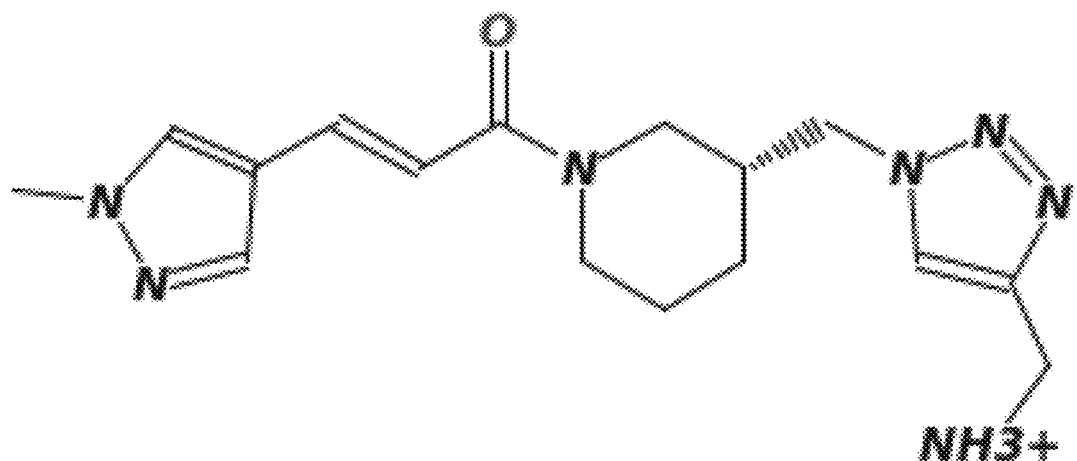
FIG. 1 shows the chemical composition of HL840.
Figure 2A:
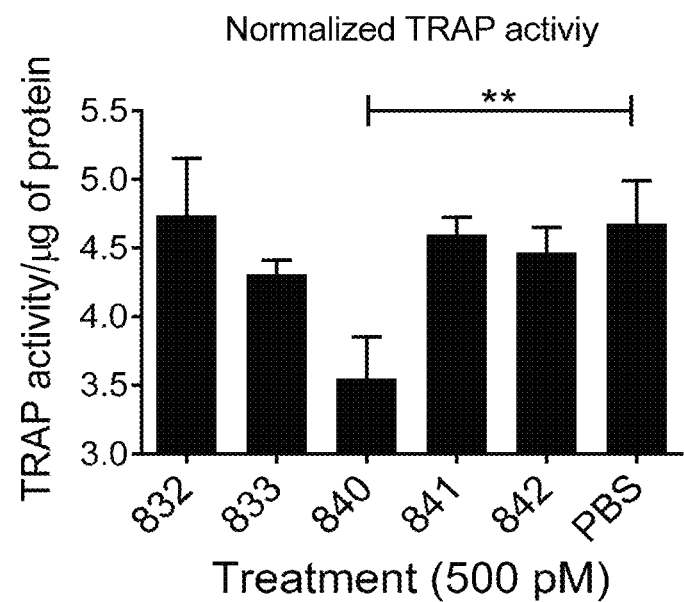
FIG. 2A shows RAW 264.7 cells cultured in osteoclast (OC)-differentiating conditions in the presence or absence of various compounds including HL840 (500 pM) and TRAP enzymatic activity measured therein.
Figure 2B:
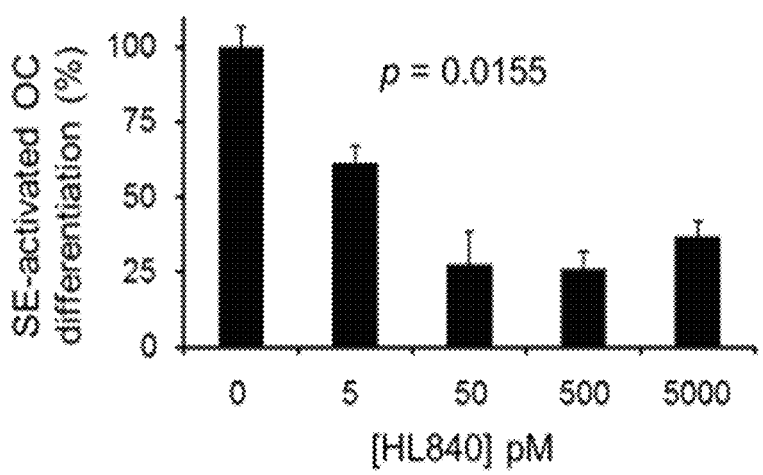
FIG. 2B shows RAW 264.7 cells cultured in OC-differentiating conditions without or with HL840 at various concentrations. OC differentiation was determined at day 5.
Figure 2C:
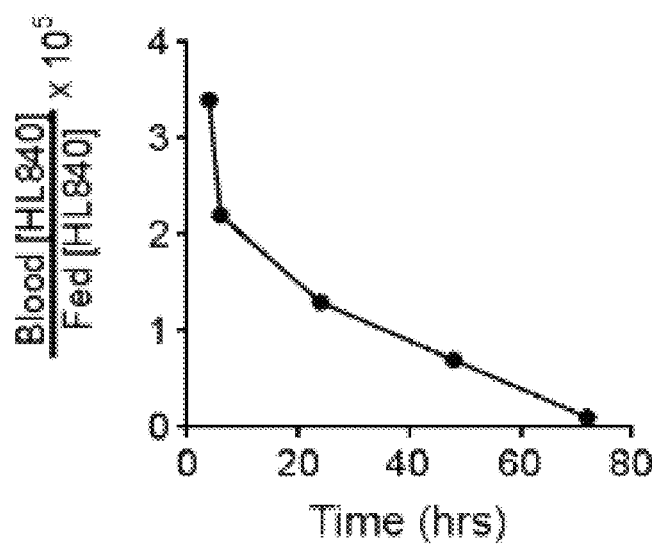
FIG. 2C shows HL840 administered by oral gavage to DBA/1 mice and serum levels determined at various time points.
Figure 2D:
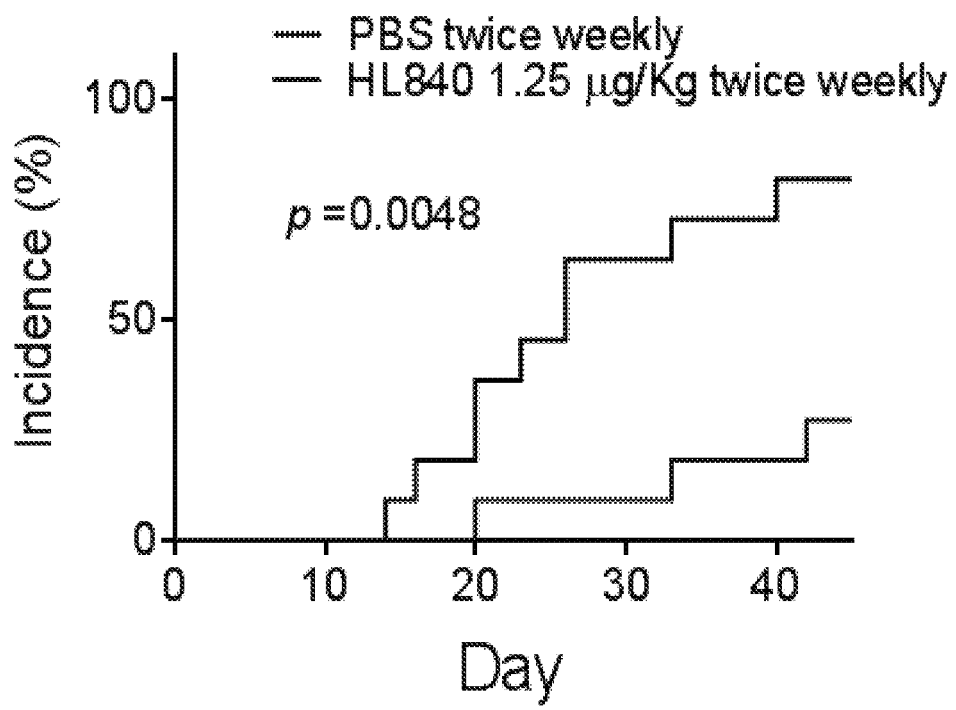
FIG. 2D shows that collagen induced arthritis (CIA) was induced in DBA/1 mice orally fed twice weekly by gavage with either PBS (black line) or HL840 (grey line) 1.25 g/Kg body weight. Arthritis incidence was recorded.
Figure 2E:
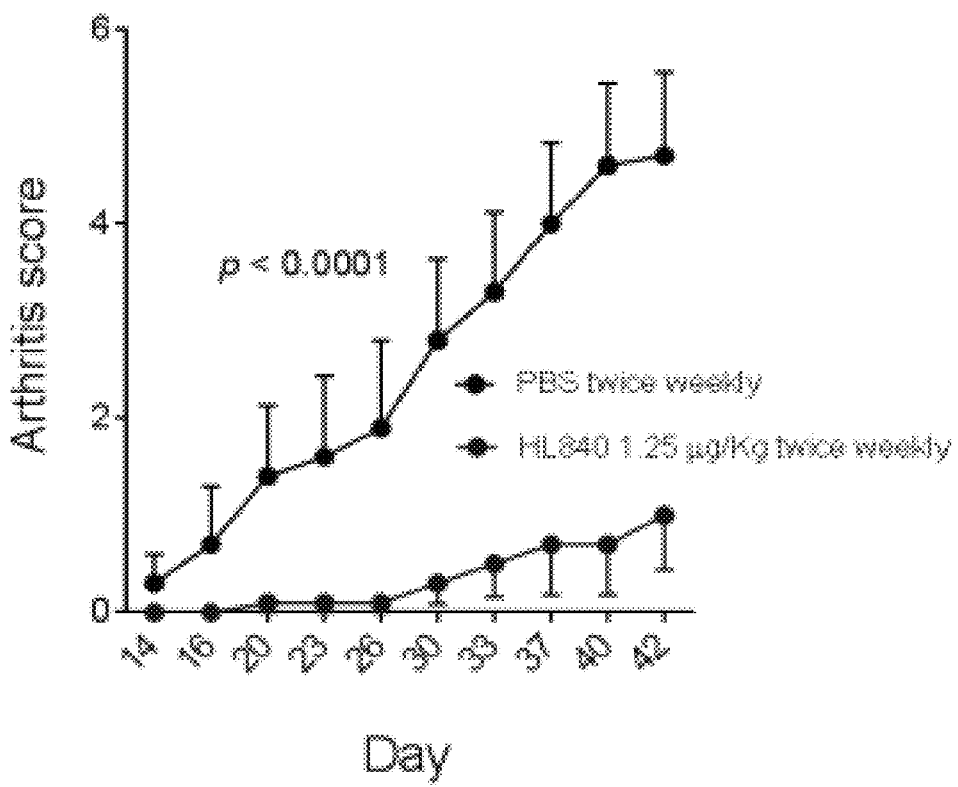
FIG. 2E shows arthritis severity in the mice shown in FIG. 2D.
Figure 2F:
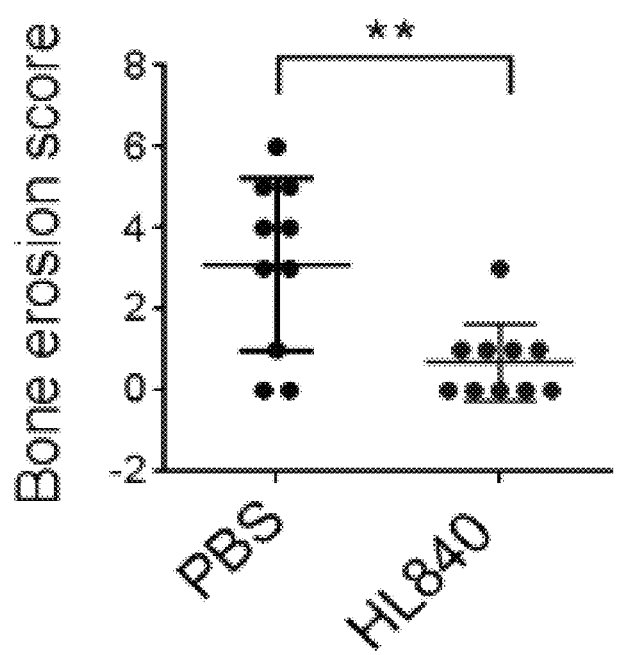
FIG. 2F shows radiologic bone damage in the mice shown in FIG. 2D. 2-tailed Student t-test; **, $p<0.005$.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent or latent defect in the organism (e.g., genetic anomalies) or to combinations of these and other factors.

The terms "host," "subject," or "patient" are used interchangeably herein to refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention.

The terms "buffer" or "buffering agents" refer to materials that when added to a solution cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution (i.e., two more protons than electrons).

The terms "chelator" or "chelating agent" refer to any materials having more than one atom with a lone pair of electrons that are available to bond to a metal ion.

The term "solution" refers to an aqueous or non-aqueous mixture.

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as an immunoregulatory disorder (e.g., rheumatoid arthritis) and/or a bone erosion disease.

As used herein, the terms "bone erosion disease," "bone erosion condition," bone remodeling disorder," "bone loss disease," and "bone loss condition" refer to any disease, disorder and/or condition that has as a symptom or sign, a disorder or deregulation of bone remodeling. Bone remodeling (or bone metabolism) is a lifelong process where mature bone tissue is removed from the skeleton (a process called bone resorption) and new bone tissue is formed (a process called ossification or new bone formation). An imbalance in the regulation of bone remodeling's two sub-processes, bone resorption and bone formation, results in or is the result of a variety of disorders of inflammatory, metabolic, pharmacologic endocrinologic, infectious, neopleastic, mecahnical and idiopathic nature. Specific examples of disease related to bone remodeling include, but are not limited to, arthritis (e.g., rheumatoid arthritis), periodontal disease, psoriatic arthritis, reactive arthritis, gout, ankylosing spondylitic, osteoarthritis, osteoporosis, anorexia nervosa, vitamin D deficiency, Cushing's syndrome, hyperparathyroidism, corticosteroids, other drug-induced osteoporosis, osteomyelitis, bone metastasis, primary bone tumors, multiple myeloma, bone fracture healing, post-surgical, prosthesis-associated bone damage, disuse, paralysis, bedridden conditions, low gravity, Paget's disease of bone, and osteonecrosis.

As used herein, "one or more signs or symptoms of rheumatoid arthritis" (RA; rheumatoid arthritis) include tender, warm, swollen joints, usually affected in a symmetrical pattern. Other symptoms of RA include fatigue and occasional fever or malaise. Pain and stiffness lasting more than 30 minutes in the morning or after a long rest are also common symptoms of RA.

As used herein, "improved" means a reduction in the severity of the signs or symptoms of a disease (e.g., RA) and a return towards normal function.

As used herein, the terms "treatment", "therapeutic use", or "medicinal use" refer to any and all uses of compositions and methods of the invention that remedy a disease state or symptoms, or otherwise prevent, hinder, retard, or reverse the progression of disease or other undesirable symptoms in any way whatsoever. Symptoms are "reduced" when the magnitude (e.g. intensity) or frequency of symptoms is reduced. In the case of RA, symptoms are reduced, for example, when the subject experiences less pain, a shorter duration of morning joint stiffness, and less swelling in the affected joints. In the case of a disease or disorder characterized by bone erosion and/or bone loss, symptoms are reduced, for example, when bone loss or bone erosion is reduced (e.g., when bone mass, bone density and/or bone structure is maintained and/or enhanced). It is not intended that the present disclosure be limited only to cases where the symptoms are eliminated. The present disclosure specifically contemplates treatment such that symptoms are reduced (and the condition of the subject is thereby "improved"), albeit not completely eliminated.

As used herein, "protecting groups" are those groups that prevent undesirable reactions (such as degradation) involving unprotected functional groups. Protecting groups can be added to the N-terminus, C-terminus or both of a small molecule and/or compound. In one embodiment, the present disclosure contemplates that the protecting group is an acyl or an amide. In one embodiment, the acyl is acetate. In another embodiment, the protecting group is a benzyl group. In another embodiment, the protecting group is a benzoyl group. The present disclosure also contemplates combinations of such protecting groups.

As used herein, "biological activity" of a small molecule and/or compound refers to the ability of the small molecule and/or compound to modulate signal transduction pathways or inhibit shared-epitope—calreticulin binding, interaction and/or activity. Activity can be assayed by a number of techniques. For example, biological activity can be assayed in an in vitro cAMP-mediated assay for DNA repair following induction of DNA damage. Biological activity can also be determined by measuring intracellular cAMP levels or protein kinase A activation following application of the small molecule/compound to cells. Biological activity may be assessed by measuring osteoclast differentiation and/or activity. Biological activity may be assessed by measuring nitric oxide signaling. Biological activity may also be assessed by measuring the activity and/or activation of T helper 17 (Th17) cells.

As used herein, "single dosage" refers to a pharmaceutical composition of a formulation that is capable of achieving its intended effect in a single application or administration (e.g., once a day, once a week, or other interval).

As used herein, the terms "administration" and "administering" refer to the act of giving a composition of the present disclosureto a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, intratumorally, etc.), topically, and the like.

As used herein, "oral administration" or "orally" refers to the introduction of a compound and/or pharmaceutical composition containing same into a subject by way of the oral cavity (e.g., in aqueous liquid or solid form).

As used herein, "sublingual administration" or "sublingually" refers to the introduction of a compound and/or pharmaceutical composition containing same into a subject by application to the mucosal surface under the tongue (within the oral cavity) such that the composition is absorbed into the subject.

As used herein, "buccal administration" or "buccal" refers to the introduction of a compound and/or pharmaceutical composition containing same into a subject by application to the mucosal surface lining the cheek (within the oral cavity) such that the composition is absorbed into the subject.

As used herein, "intranasal administration" or "intranasally" refers to the introduction of a compound and/or pharmaceutical composition containing same within the nasal cavity.

As used herein, "respiratory inhalation" refers to the introduction of a compound and/or pharmaceutical composition containing same within the respiratory tract.

As used herein, "intrapulmonary delivery" refers comprises administration to the lung. Intrapulmonary delivery of pharmacologic agents to patients can be accomplished via aerosolization. Alternatively, the agent may be administered to the lung through a bronchoscope.

As used herein, "transdermal administration" or "transdermally" or "cutaneously" refers to the introduction of a compound and/or pharmaceutical composition containing same into a subject by application to the surface of the skin such that the composition is absorbed into the subject.

As used herein, "injection" or "standard injection" refers to the placement of a compound and/or pharmaceutical composition containing same into a subject (e.g., with a hypodermic needle). For example, such injection can be made subcutaneously, intravenously, intramuscularly, intracavernosally, etc.

As used herein, "intra-articular" injection refers to direct injection of a compound and/or pharmaceutical composition containing same into a joint (for example, in a method of treatment of RA).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present disclosure. A "known therapeutic compound" refers to a therapeutic compound that has been shown (e.g., through animal trials or prior experience with administration to humans) to be effective in such treatment or prevention.

As used herein, the term "effective amount" refers to the amount of a compound and/or pharmaceutical composition containing same (e.g., a compound of the present disclosure) sufficient to effect beneficial or desired results. An effective amount can be administered in one or more administrations, applications or dosages and is not intended to be limited to a particular formulation or administration route.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of an immunoregulatory abnormality (e.g., autoimmune disease or chronic inflammatory disease (e.g., rheumatoid arthritis)), in one embodiment, a therapeutically effective amount will refer to the amount of a therapeutic agent that inhibits, reduces, decreases and/or reverses bone erosion, bone mass loss, bone density loss, and/or bone structure loss in the subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

As used herein, the term "co-administration" refers to the administration of at least two agent(s) (e.g., a compound of the present disclosure and another active agent) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The terms "sensitize" and "sensitizing," as used herein, refer to making, through the administration of a first agent, an animal or a cell within an animal more susceptible, or more responsive, to the biological effects (e.g., promotion or retardation of an aspect of cellular function) of a second agent. The sensitizing effect of a first agent on a target cell can be measured as the difference in the intended biological effect (e.g., inhibition of bone erosion) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the term "pharmaceutically acceptable salt" refers to any salt (e.g., obtained by reaction with an acid or a base) of a composition of the present disclosurethat is physiologically tolerated in the target subject. "Salts" of the compositions of the present disclosuremay be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula NW4+, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosurecompounded with a suitable cation such as Na+, NH4+, and NW4+ (wherein W is a C1-4 alkyl group), and the like. For therapeutic use, salts of the compounds of the present disclosureare contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present disclosureare contemplated as being pharmaceutically acceptable. However, salts of acids and bases that are non-pharmaceutically acceptable may also find use, for example, in the preparation or purification of a pharmaceutically acceptable composition.

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

As used herein, the term "kit" refers to any delivery system for delivering materials. In the context of compounds of the invention, such delivery systems include systems that allow for the storage, transport, and/or delivery of the compounds and/or supporting materials (e.g., written instructions for using the materials, etc.) from one location to another. For example, kits include one or more enclosures (e.g., boxes) containing the relevant compounds. As used herein, the term "fragmented kit" refers to delivery systems comprising two or more separate containers that each contain a subportion of the total kit components. The containers may be delivered to the intended recipient together or separately. For example, a first container may contain a composition comprising a compound for a particular use, while a second container contains a second agent (e.g., an anti-inflammatory or anti-rheumatic agent). Indeed, any delivery system comprising two or more separate containers that each contains a subportion of the total kit components are included in the term "fragmented kit." In contrast, a "combined kit" refers to a delivery system containing all of the components needed for a particular use in a single container (e.g., in a single box housing each of the desired components). The term "kit" includes both fragmented and combined kits.

DETAILED DESCRIPTION OF THE INVENTION

Osteoclast (OC)-mediated bone damage is a common, devastating outcome in rheumatoid arthritis (RA) (Bromley et al., 1984 Arthritis Rheum. 27: 857-863; Gravallese et al., 2000. Arthritis Rheum. 43: 250-258). Despite the advent of biologic agents, treating erosive RA remains a challenging endeavor due to insufficient understanding of the mechanisms that specifically trigger RA disease onset and determine its severity. Most current and emerging drugs are targeted at generic immune-modulating pathways or inflammatory cytokines. As a result, drug failure and/or side effects are common.

While the pathogenesis of RA is not well understood, it has been long observed that the majority of RA patients carry HLA-DRB1 alleles coding a five amino acid sequence motif called the 'shared epitope' (SE) in the region 70-74 of the DRβ chain (Gregersen et al., 1987. Arthritis Rheum. 30: 1205-1213). The SE not only confers a higher risk for RA, but also increases the likelihood of developing a more severe disease. SE-coding HLA-DRB1 alleles are associated with earlier disease onset and more severe bone erosions (Gonzalez-Gay et al., 2002. Semin. Arthritis Rheum. 31: 355-360; Matey et al., 2001. Arthritis Rheum. 44: 1529-1533; Plant et al., 1998 J. Rheumatol. 25: 417-426; Weyand et al., 1994. J. Lab. Clin. Med. 124: 335-338). Furthermore, there is evidence of gene-dose effect, where the extent of bone destruction in RA correlates positively with the number of SE-coding HLA-DRB1 alleles (Matey et al., supra; Plant et al., supra; Weyand et al.,supra).

SE functions as a signal transduction ligand that binds to cell surface calreticulin (CRT) in a strictly allele-specific manner and activates nitric oxide (NO)-mediated pro-oxidative signaling (Ling et al., 2006. Arthritis Rheum. 54: 3423-3432; Ling et al., 2007. Arthritis Res Ther 9: R5; Ling et al., 2007. The Journal of Immunology 179: 6359-6367; Ling et al., 2012 Arthritis Rheum.; De Almeida et al., 2010. The Journal of Immunology 185: 1927-1934; Holoshitz et al., 2010 Ann. N. Y. Acad. Sci. 1209: 91-98; U.S. Pat. Nos. 7,208,154; 7,074,893). One of the functional consequences of SE ligand-activated signaling is expansion of IL-17-producing T (Th17) cells, both in vitro and in vivo (De Almeida et al., supra)).

Th17 cells are central players in arthritis pathogenesis (Shahrara et al., 2008 Arthritis Res Ther 10: R93). These cells have been previously shown to express high levels of the receptor activator for nuclear factor-κB (RANK) ligand (RANKL) and activate osteoclastogenesis (Sato et al., 2006 J. Exp. Med. 203: 2673-2682; Kotake et al., 1999 J. Clin. Invest. 103: 1345-1352). In previous studies, it was demonstrated that the SE ligand facilitates osteoclast (OC) differentiation in mouse and human cells in vitro and enhanced the differentiation of RANKL-expressing Th17 cells. When administered in vivo to mice with collagen-induced arthritis (CIA), the SE ligand increased joint swelling, synovial tissue OC abundance and erosive bone damage (Holoshitz et al., 2012, J. Immunol).

Given that the SE acts as a signal transduction ligand that directly contributes to arthritis severity, experiments were conducted during development of embodiments of the invention in order to identify and characterize ways to inhibit this pathway.

Targeting the SE-CRT pathway provides an additional advantage over the prevailing therapeutic paradigms due to the unique role played by this pathway at an upstream phase in RA pathogenesis. The SE is the single most significant risk factor for RA. It determines susceptibility, severity and even disease penetrance in monozygotic twins (Jawaheer et al., 1994 Arthritis Rheum. 37: 681-686). Thus, different from effector cytokines or enzymes involved in lymphocyte activation, this pathway is intimately involved in disease etiology and early genesis.

Experiments conducted during development of embodiments of the invention identified HL840

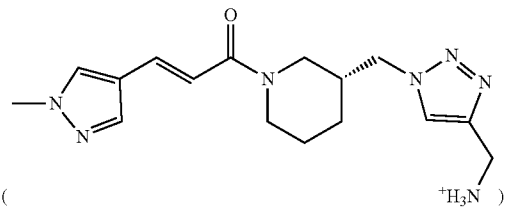

((R,E)-(1-((1-(3-(1-methyl-1H-pyrazol-4-yl)acryloyl)piperidin-3-yl)methyl)-1H-1,2,3-triazol-4-yl)methanaminium) as a moderately orally available, potent anti-OC small molecule that displays strong anti-arthritis and anti-bone erosion effects in vivo when administered orally to mice with pre-clinical models of RA (See, e.g., Examples 1-3).

Figure 3:
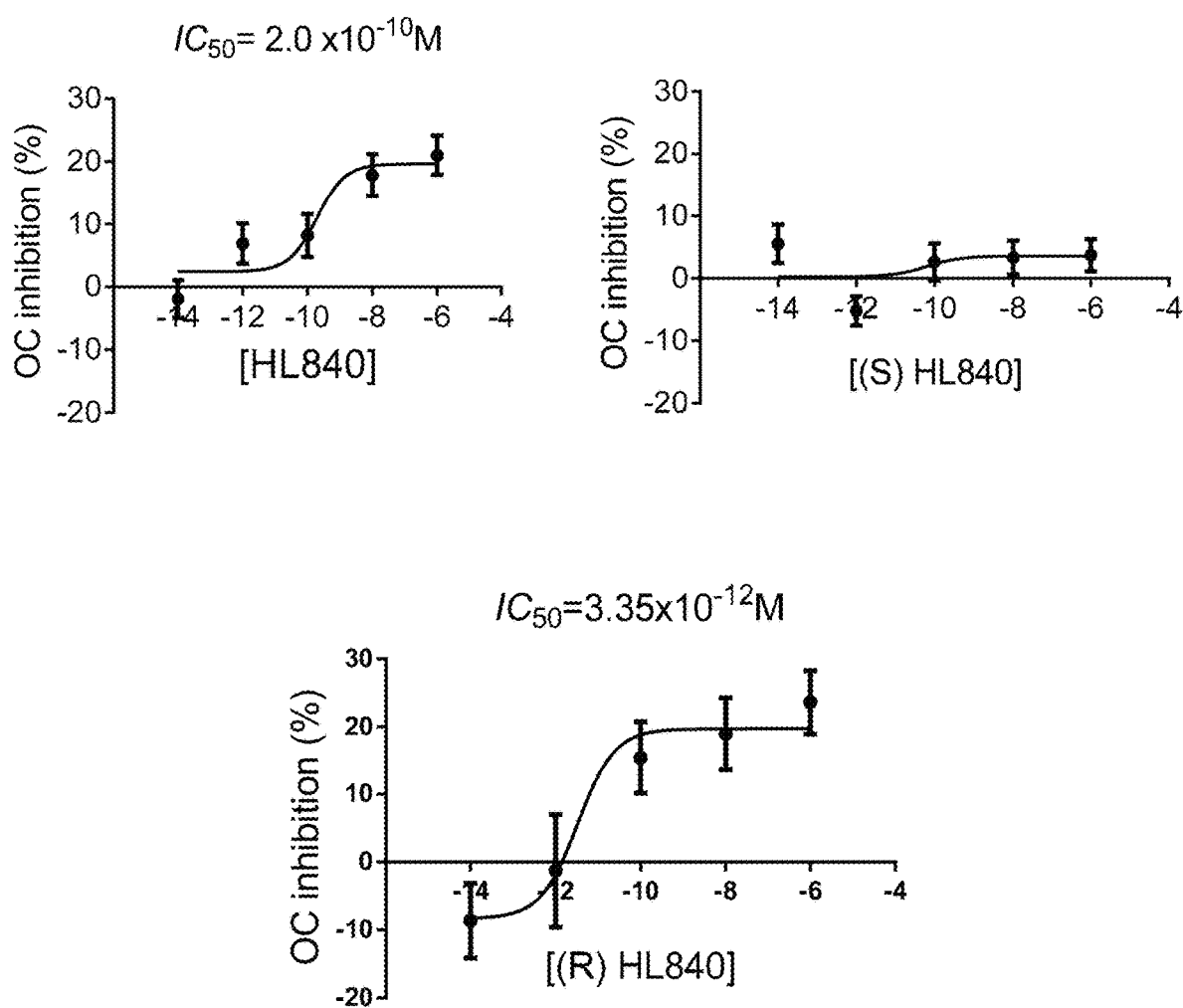
FIG. 3 shows the enantiomer-specificity of HL840. RAW 264.7 cells were cultured in OC-differentiating conditions in the presence or absence of the racemic mix (left) of HL840, the S-enantiomer (middle), or the R-enantiomer (right) at different concentrations, and their inhibitory effect on OC differentiation was determined at day 5.

Further experiments were performed in order to determine if the enantiomers of HL840 displayed different pharmacological properties including potency and metabolic stability. Novel synthesis schemes were generated in order to synthesize the racemate and both enantiomers. As shown in FIG. 3, the (R)-enantiomer was responsible for all activity (e.g., inhibition of SE-CRT interaction and signaling) of racemic HL840.

Further experiments identified additional small molecules having a triazole-methyl-piperidinyl-pyrolyl-propenone structure and structurally similar which function as modulators of shared epitope (SE)—calreticulin (CRT) binding and/or interaction (see, e.g., Example 4 and FIG. 6).

Accordingly, the invention relates to a new class of small-molecules having a triazole-methyl-piperidinyl-pyrolyl-propenone structure which function as modulators of shared epitope (SE)—calreticulin (CRT) binding and/or interaction, and their use as therapeutics for the treatment of immunoregulatory abnormalities (e.g., autoimmune diseases, inflammatory diseases (e.g., chronic inflammatory disease), and bone erosive diseases) by selectively inhibiting SE-CRT interactions and/or signal transduction pathways commonly overactive or dysregulated in arthritic and/or other diseases or conditions.

In a particular embodiment, triazole-methyl-piperidinyl-pyrolyl-propenone compounds and structurally similar compounds encompassed within Formulas I, II, III, and IV are provided:

(Formula I)
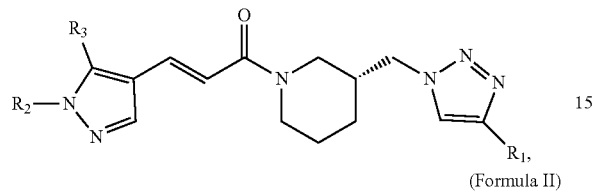

(Formula II)
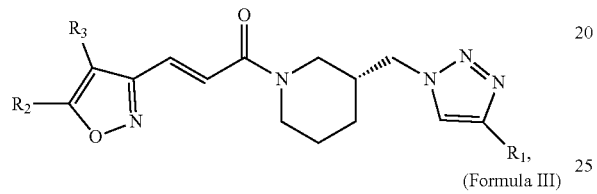

(Formula III)
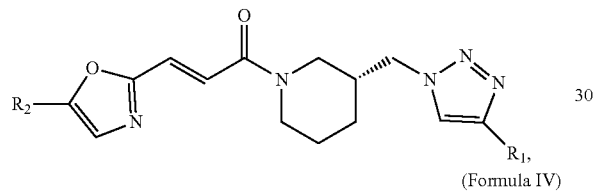

(Formula IV)
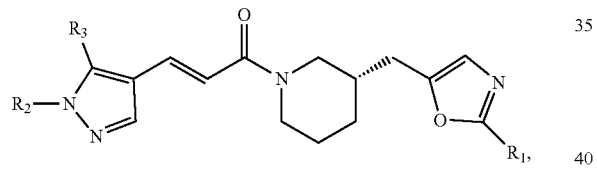

including pharmaceutically acceptable salts, solvates, and/or prodrugs thereof.

Formulas I, II, III and IV are not limited to a particular chemical moiety for R1, R2, and R3. In some embodiments, the particular chemical moiety for R1, R2, and R3 independently include any chemical moiety that permits the resulting compound to modulate of SE-CRT binding and/or interaction.

In some embodiments, R1 is

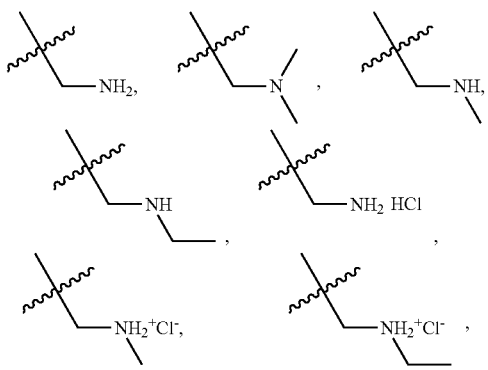

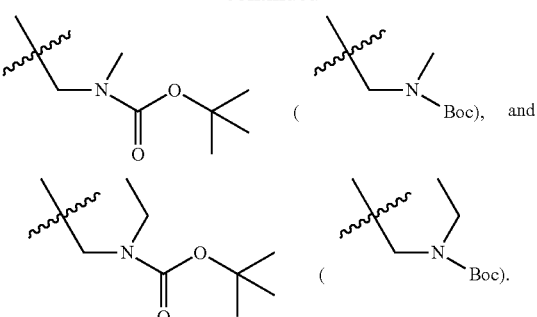

In some embodiments, R2 is $CH_3$,

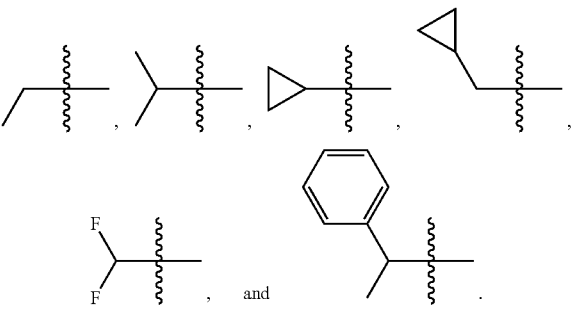

In some embodiments, R3 is hydrogen or fluorine.

In some embodiments, the following compounds are contemplated for Formulas I, II, III and IV:

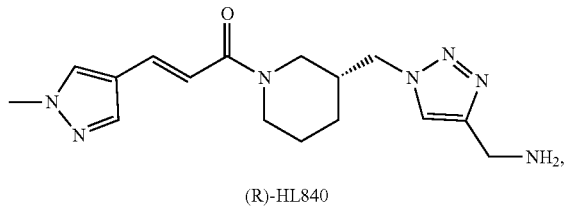
(R)-HL840

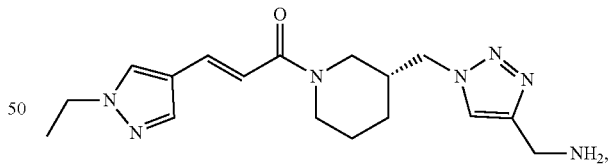

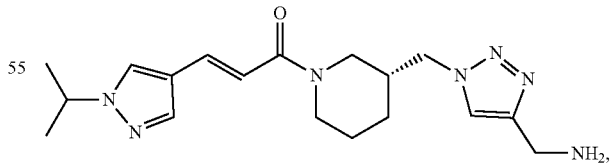

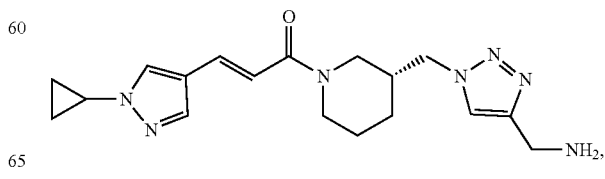

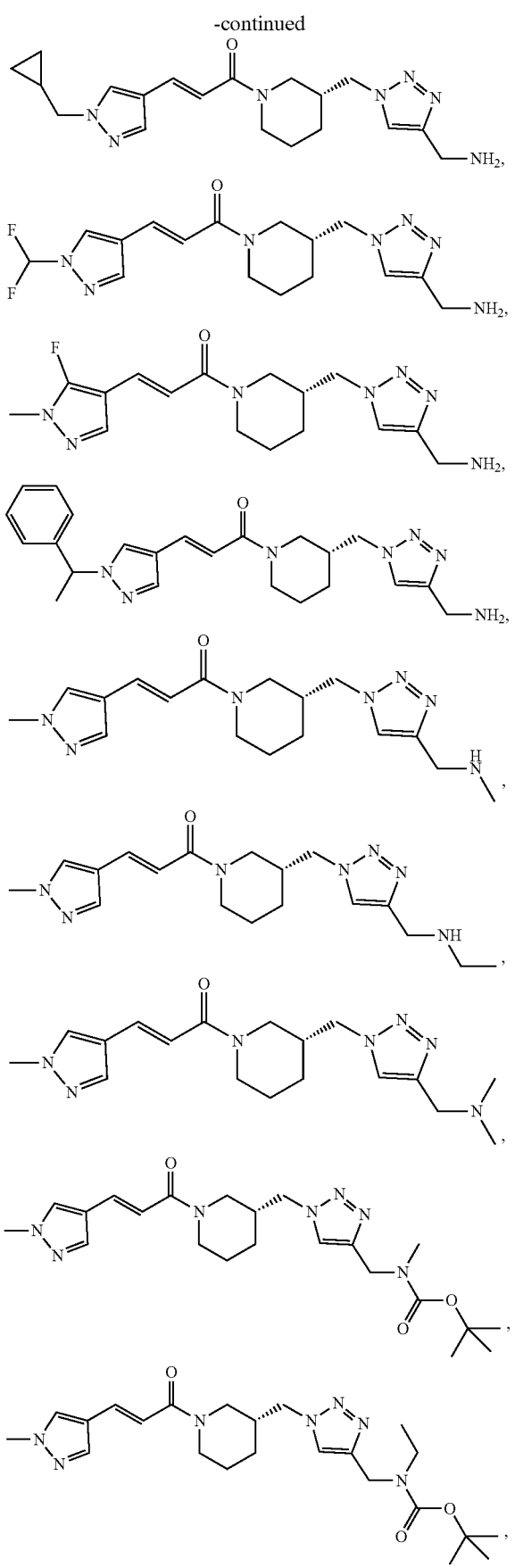

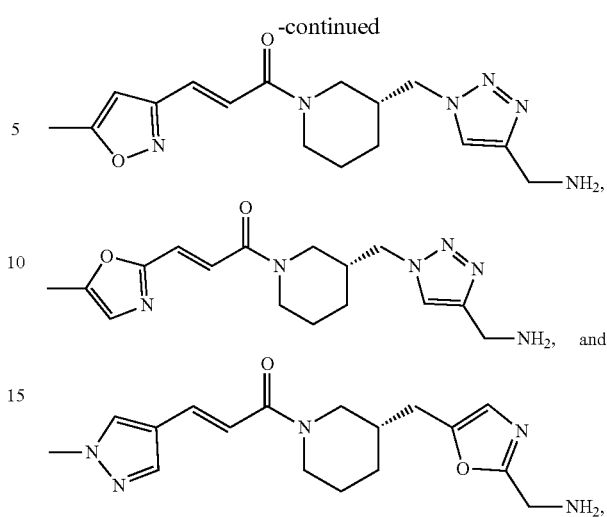

, or a pharmaceutically acceptable salt, solvate, or prodrug thereof.

Figure 4:
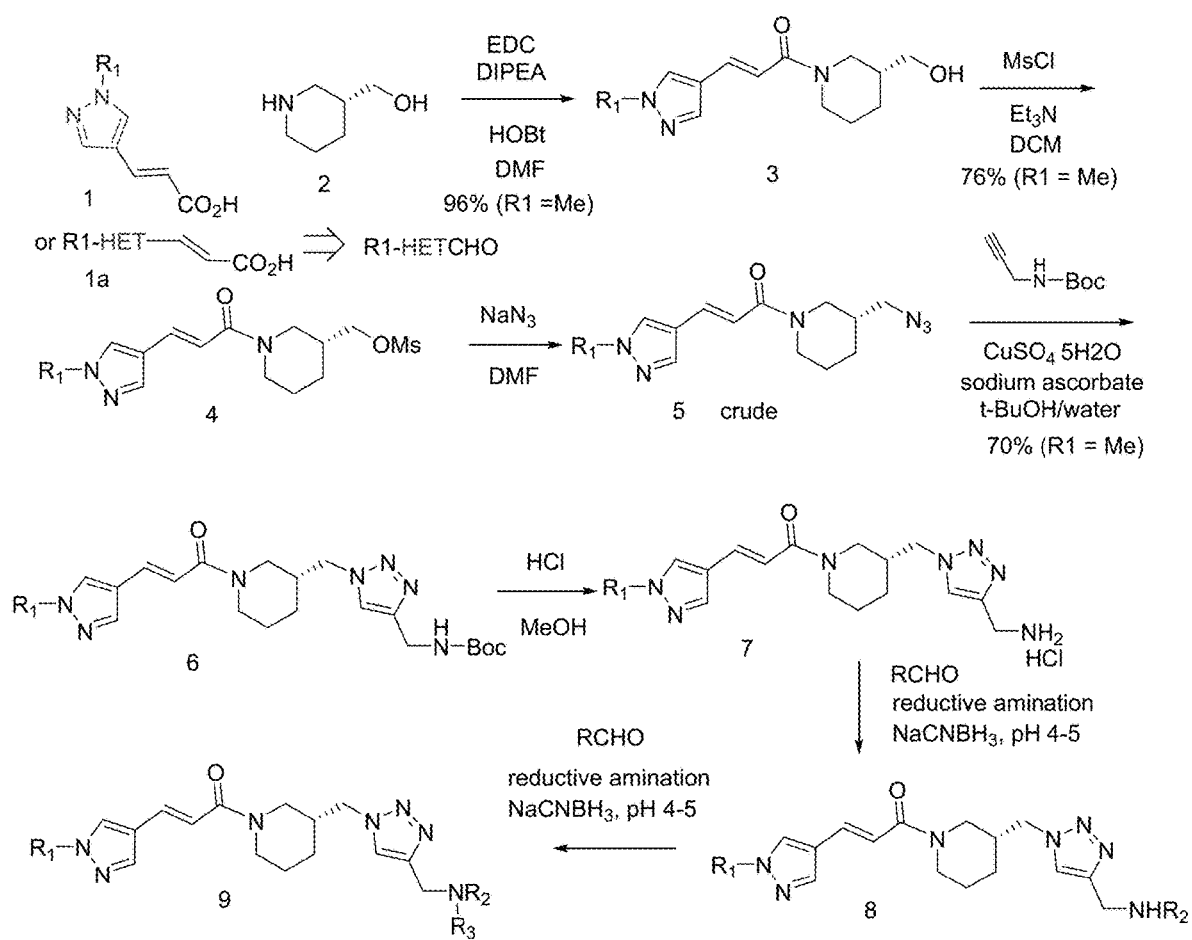
FIG. 4 shows the synthesis scheme for (R)-HL840 in one embodiment of the invention.

The disclosure therefore provides a compound ((R)-HL840, shown in FIGS. 1 and 4) and additional compounds (Example 4 and FIG. 6) that are highly potent inhibitors of SE-CRT interactions and osteoclast activation. Thus, in one embodiment and as described in detail herein, the invention provides such compounds and compositions (e.g., pharmaceutical compositions) comprising same, for use in treating or delaying the progression of an immunoregulatory abnormality (e.g., caused by SE-CRT signaling and/or osteoclast activation (e.g., rheumatoid arthritis and/or other bone-destroying diseases)). Such compounds displayed acceptable permeability characteristics and was orally available in vivo (See Examples 1 and 4).

The invention provides, in one embodiment, pharmaceutically acceptable salts of (R)-HL840 (and structurally similar compounds (see, Example 4 and FIG. 6)) generally derived by dissolving the free acid or the lactone; preferably the lactone, in aqueous or aqueous alcohol solvent or other suitable solvents with an appropriate base and isolating the salt by evaporating the solution or by reacting the free acid or lactone; preferably the lactone and base in an organic solvent in which the salt separates directly or can be obtained by concentration of the solution. In practice, use of the salt form amounts to use of the acid or lactone form. Appropriate pharmaceutically acceptable salts within the scope of the invention are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like. Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of (R)-HL840 will give the calcium salt thereof.

Generally, (R)-HL840 and related analogs of the present disclosure can be prepared by a synthesis scheme as shown in FIG. 4. One of ordinary skill in the art would recognize variations in the scheme which are appropriate for the preparation of the compounds of the present invention. Accordingly, in one embodiment, the present disclosure provides a pharmaceutical composition prepared from (R)-HL840 or related analog, (e.g., as shown in FIG. 4 or FIG. 5, respectively), or pharmaceutically acceptable salts thereof.

An important aspect of the present invention is that compounds of the invention satisfy an unmet need for the treatment of immunoregulatory abnormalities (e.g., autoimmune diseases, inflammatory diseases (e.g., chronic inflammatory disease), and bone erosive diseases), either when administered as monotherapy, or when administered in a temporal relationship with additional agent(s), such as other pharmaceutical agents known to be effective in treating such conditions or symptoms related to such conditions (combination therapies) through inhibiting SE-CRT binding and/or interaction.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. Indeed, the invention provides methods of treating an immunoregulatory abnormality in a subject (e.g., a mammalian patient) in need of such treatment comprising administering to the patient a compound of the invention in an amount that is effective for treating the immunoregulatory abnormality. The invention is not limited to any particular immunoregulatory abnormality. In one embodiment, the immunoregulatory abnormality is an autoimmune disease. In another embodiment, the immunoregulatory abnormality is a chronic inflammatory disease. In one embodiment, the autoimmune disease or chronic inflammatory disease is rheumatoid arthritis. In one embodiment, the treatment inhibits and/or reduces bone erosion in the subject. Other immunoregulatory abnormalities may be treated including, but not limited to transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C.sub.4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

In yet another embodiment, the invention provides methods of suppressing the immune system in a subject (e.g., mammalian patient) in need of immunosuppression comprising administering to the patient an immunosuppressing effective amount of a compound of the invention. In a further embodiment, a compound of the invention is combined with a pharmaceutically acceptable carrier (e.g., to generate a pharmaceutical composition). Compounds of the invention, and pharmaceutical compositions comprising same, find use in methods of treating a disease or condition characterized with bone erosion and/or bone loss in a subject (e.g., a mammalian patient) comprising administering to the subject (e.g., patient) a composition (e.g., a pharmaceutical composition) of the invention in an amount that is effective for treating the bone erosion and/or bone loss disease or condition. The invention is not limited by the type of bone loss disease or condition treated. Indeed, a variety of bone loss diseases or conditions may be treated including, but not limited to, rheumatoid arthritis, a bone destroying arthritic condition, periodontal disease, osteoporosis, osteomyelitis, bone metastasis, bone fracture healing, or other disease or condition in which bone loss and/or bone erosion is present.

In yet another embodiment, compositions and methods of the invention can be used in methods of treatment of a subject (e.g., a mammalian patient) to enhance and/or maintain bone density, bone mass, and/or bone structure.

Some embodiments of the present invention provide methods for administering an effective amount of a compound of the invention and at least one additional therapeutic agent (including, but not limited to, anti-inflammatory agents and/or anti-rheumatic agents). Examples of anti-inflammatory agents and/or anti-rheumatic agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In some embodiments of the present invention, a compound of the invention and one or more therapeutic agents (anti-inflammatory agents and/or anti-rheumatic agents) are administered to an animal under one or more of the following conditions: at different periodicities, at different durations, at different concentrations, by different administration routes, etc. In some embodiments, the compound is administered prior to the therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic agent. In some embodiments, the compound is administered after the therapeutic agent, e.g., 0.5, 1, 2, 3, 4, 5, 10, 12, or 18 hours, 1, 2, 3, 4, 5, or 6 days, or 1, 2, 3, or 4 weeks after the administration of the therapeutic agent. In some embodiments, the compound and the therapeutic agent are administered concurrently but on different schedules, e.g., the compound is administered daily while the therapeutic agent is administered once a week, once every two weeks, once every three weeks, or once every four weeks. In other embodiments, the compound is administered once a week while the therapeutic agent is administered daily, once a week, once every two weeks, once every three weeks, or once every four weeks.

The compounds of the present disclosure (e.g., utilized in pharmaceutical compositions and methods of using the same described herein) can be administered to a patient at dosage levels of from 70 μg to 500 mg per day which for a normal human adult of approximately 70 kg is a dosage of from 1 μg/kg to 7.1 mg/kg of body weight per day. The dosages may be preferably from 0.1 to 1.0 mg/kg per day. Any patient that would benefit from inhibition of SE-CRT interaction and/or inhibition of osteoclast activation may benefit from administration of the compounds and compositions described herein. Indeed, any immunoregulatory abnormality (e.g., caused by SE-CRT interaction and/or signaling or by aberrant osteoclast activation) can be treated with such compounds and compositions.

The dosage is preferably administered as a unit dosage form. The unit dosage form for oral or parenteral use may be varied or adjusted (e.g., from 10 to 500 mg, preferably from 20 to 100 mg) according to the particular application and the potency of the active ingredient(s). Compositions of the invention, if desired, may contain other active therapeutic agents (e.g., anti-inflammatory and/or anti-rheumatic agent(s)). Determinations of optimum dosages (e.g., therapeutically effective amounts) for a particular situation is within the skill of one of ordinary skill in the art.

Embodiments of the present disclosure further provide the compounds described herein for use in research, screening, and therapeutic applications.

For example, the present disclosure also provides methods of modifying and derivatizing the compositions of the present disclosure to increase desirable properties (e.g., binding affinity, activity, solubility and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

The present disclosure is not limited by the method of introduction of the compounds and compositions (e.g., therapeutic compound and composition) to the body. Among other methods, the present disclosure contemplates administering orally, cutaneously, or by standard injection (e.g. intravenous).

The present disclosure also contemplates administering the compounds described herein to a patient intranasally or through respiratory inhalation. Formulations suitable for intranasal administration include ointments, creams, lotions, pastes, gels, sprays, aerosols, oils and other pharmaceutical carriers which accomplish direct contact between the compounds of the disclosure or a pharmaceutical composition comprising compounds of the disclosure and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all herein incorporated by reference. Formulations suitable for respiratory inhalation include ointments, creams, lotions, pastes, gels, sprays, aerosols, oils and other pharmaceutical carriers which accomplish direct contact between compounds of the disclosure or a pharmaceutical composition comprising compounds of the disclosure and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all herein incorporated by reference.

In some embodiments, intranasal administration and respiratory inhalation are used due to the ease of administration and faster onset of therapeutic activity. It is contemplated that intranasal administration and respiratory inhalation may be advantageous as they may allow a smaller effective dosage to be administered than would be possible with the oral route of administration. Another mode of administration comprises administration to the lung. Intrapulmonary delivery of pharmacologic agents to patients can be accomplished via aerosolization. Alternatively, the agent may be administered to the lung through a bronchoscope.

The disclosure is not limited by the form of oral administration of aqueous and/or organic solutions of the compounds described herein. Likewise, compounds of the disclosure can be associated with a solid pharmaceutical carrier for solid oral administration (e.g., in pill form). One skilled in the art is able to readily prepare such solid formulations, and in one non-limiting embodiment, the inactive ingredients include croscarmellose sodium, hydroxypropyl methylcellulose, lactose, magnesium stearate, methocel E5, microcrystalline cellulose, povidine, propylene glycol and/or titanium dioxide.

The compounds described herein may also be administered cutaneously in a carrier adapted for topical administration. Such carriers include creams, ointments, lotions, pastes, jellies, sprays, aerosols, bath oils, or other pharmaceutical carriers that accomplish direct contact between the compounds of the disclosure and the pore of the skin. In general pharmaceutical preparations may comprise from about 0.001% to about 10%, and preferably from about 0.01 to 5% by w/w of the active compound. In some cases it may be useful to dissolve the active compound in an appropriate solvent such as ethanol or DMSO (dimethylsulfoxide), and the like, to facilitate incorporation into a pharmaceutical preparation.

While the present disclosure is not limited by a specific method of introducing compounds of the disclosure by injection, injection of the compounds of the disclosure can be carried out by any conventional injection means (e.g., employing an hypodermic syringe and needle or a similar device such as the NovolinPen sold by Squibb-Novo, Inc., Princeton, N.J., USA). Injection may be by the subject injecting him or herself or by another person injecting the patient.

The compounds described herein can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in compositions and methods of the invention is physiological saline or phosphate buffered saline, in which compounds of embodiments of the present disclosure are dissolved or suspended, such that the resulting composition is suitable for injection. Such a physiologically acceptable composition can also include a non-irritant preservative, such as, e.g., benzalkonium chloride at 0.05% (w/v) to 0./2% (w/v).

While the present disclosure is not limited to the method of injecting compounds, in some embodiments, it is injected with a standard syringe. One skilled in the art is capable of injecting compounds of the present disclosure with a carrier as described above.

In some embodiments (e.g. in a method of treating a subject with symptoms of RA), it is desirable that the compositions of the disclosure reach the affected joints. In some embodiments, this may be accomplished by cutaneous or transdermal application of pharmaceutical compositions comprising the compounds described herein directly to the skin over the affected joint. In other embodiments, delivery of the compounds to the affected joints may be by direct injection into the joint. The present disclosure specifically contemplates intra-articular injections (e.g., into a specific joint to be treated (e.g., knee, shoulder, acromioclavicular joint, sternoclavicular joint, ankle joint, subtalar ankle joint, wrist, first carpometacarpal joint, metacarpophalalangeal joints, finger interphalangral joints, metatarsophalangeal joints and toe interphalangeal joints, elbow, hip, temporomandibular joint, and/or other joint that would benefit from treatment)).

As described herein, embodiments of the present disclosure provide compositions and methods for treating a variety of autoimmune disease, including but not limited to, rheumatoid arthritis (RA). In some embodiments, compounds (e.g., compounds and/or pharmaceutical compositions comprising same described herein) are administered to subjects diagnosed with RA. In some embodiments, the administration reduces or eliminates one or more symptoms of RA. In some embodiments, administration prevents or reverses bone damage caused by RA.

In some embodiments, compounds (e.g., compounds and/or pharmaceutical compositions comprising same described herein) are administered once to a subject in need thereof. In other embodiments, compositions are administered on an ongoing, recurrent, or repeat basis (e.g., multiple times a day, once a day, once every 2, 3, 4, 5, or 6 days, once a week, etc.) for a period of time (e.g., multiple days, weeks, months, or years). Suitable dosages and dosing schedules are determined by one of skill in the art using suitable methods (e.g., those described in the experimental section below or known to one of skill in the art).

In some embodiments, the present disclosure provides methods of treating a disease and/or disorder characterized as involving bone erosion, bone loss, and/or deregulated bone remodeling. Examples include, but are not limited to, inflammatory disease or disorder (e.g., arthritis (e.g., rheumatoid arthritis), periodontal disease, psoriatic arthritis, reactive arthritis, gout, SLE, ankylosing spondylitic, osteoarthritis), metabolic disease or disorder (e.g., osteoporosis, anorexia nervosa), pharmacologic disease or disorder (e.g., corticosteroids, other drug-induced osteoporosis), endocrine disease or disorder (e.g., vitamin D deficiency, Cushing's syndrome, hyperparathyroidism), infectious disease (e.g., osteomyelitis), neoplastic disease or disorder (e.g., bone metastasis, primary bone tumors, multiple myeloma), mechanical disorder (e.g., bone fracture healing, post-surgical, prosthesis-associated bone damage, disuse, paralysis, bedridden condition) and idiopathic disease or disorder (e.g., Paget's disease of bone, osteonecrosis).

The invention also provides kits comprising a medicament comprising a compound of the invention (e.g., independently or in combination with a pharmaceutically acceptable carrier), and a package insert comprising instructions for administration of the medicament for treating or delaying progression of bone erosion and/or bone loss in a mammalian patient. The kits may optionally contain other therapeutic agents, e.g., anti-inflammatory agents and/or anti-rheumatic agents.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

HL840 Inhibits SE-CRT Interactions and Signaling

As described in detail herein, shared epitope (SE) ligand binds to calreticulin (CRT) and activates aberrant immune system signaling/regulation.

Experiments were conducted during development of embodiments of the invention in order to identify and characterize chemical compounds able to inhibit SE-CRT binding and/or immune signaling activation. HL840 (See FIG. 1) was identified and displayed potent, competitive inhibition of SE-CRT interactions. As shown in FIG. 2, HL840 was tested in vitro for its anti-osteoclast (OC) activity using an in vitro OC differentiation assay. HL840 displayed potent ($IC_{50}=1.99\times10^{-11}$ M) anti-osteoclast (OC) activity and also displayed desirable permeability characteristics (permeability through Caco-2 cell layers ($Papp_{A-B}=5.6\times10^{-6}$ cm/s). Additional experiments indicated that HL840 is orally available in vivo.

Specifically, experiments were conducted with an animal model of collagen induced arthritis (CIA). When administered orally to mice with CIA (at doses as low as 1.25 µg/Kg body weight twice weekly), HL840 strongly inhibited disease development, decreased arthritis severity and prevented bone destruction (See FIG. 2). Significant therapeutic effects were also observed in another pre-clinical model of RA in SKG mice.

Example 2

HL840 Enantiomer-Specific Effects

HL840 is commercially available as a racemate. Experiments were performed in order to determine if the enantiomers of HL840 displayed different pharmacological properties including potency and metabolic stability. Accordingly, the racemate and both enantiomers were synthesized via novel synthetic routes (See Example 3, below, and FIG. 4). As shown in FIG. 3, the (R)-enantiomer was responsible for all activity (e.g., inhibition of SE-CRT interaction and signaling) of the racemic HL840.

Example 3

Chiral Synthesis of (R)-HL840 and Related Analogs

The synthesis of (R)-HL840 (R1=Me, R2=H) is shown in FIG. 4. This route is very amenable to analog synthesis. Commercially available chiral piperidin-3-ylmethanol 2 was coupled with the pyrazole acrylic acid 1 to afford the amide 3. Many heterocyclic isosteres for pyrazole (e.g ioxazole, oxazole) are commercially available as the appropriate acrylic acid regioisomer (e.g. 1a in FIG. 4). Various substituted acrylic acids can also be synthesized from commercially available aldehydes R1HETCHO. Mesylation of the alcohol 3 to afford 4 and displacement with azide afforded crude 5. The azide 5 can then be subjected to a 3+2 cyclization with a commercially available Boc protected substituted alkyne to afford the 1,2,3 triazole 6. Removal of the Boc under standard conditions affords analogs 7. Subsequent sequential reductive amination with aldehydes affords analogs 8 and 9 respectively.

Additional analogues may be synthesized utilizing the same or similar schemes. For example, in addition to (R)-HL840 shown in FIG. 4, additional R1 groups and left hand side heterocyclic isosteres (e.g., as many are commercially available) may be used to generate related analogues (See, e.g., analogues shown in FIG. 5).

Example 4

Small Molecules Having a triazole-methyl-piperidinyl-pyrolyl-propenone Structure and Structurally Similar Inhibit Osteoclast Formation Experiments identified additional small molecules having a triazole-methyl-piperidinyl-pyrolyl-propenone structure and structurally similar which function as modulators of shared epitope (SE)—calreticulin (CRT) binding and/or interaction.

To differentiate osteoclast (OC) from RAW 264.7 mouse macrophages, cells were cultured in the same way ($2\times10^4$ per well), except that RANKL was added at a concentration of 20 ng/ml, for 5-6 days in the presence or absence of various compounds at different concentrations. To quantify the number of OCs, cultures were fixed and stained for tartrate-resistant acid phosphatase (TRAP) activity using an acid phosphatase kit (Kamiya Biomedical Company, Seattle, WA) according to the manufacturer's instructions. TRAP-positive multinucleated OCs (>3 nuclei) were counted using a tissue culture inverted microscope. All experiments were performed in triplicates and repeated 4 (C & D, n=12) or 3 (E-L; n=9) times. Percent inhibition of OC formation relative to cultures with PBS were calculated and presented as dose-response curves. IC50 values were calculated using the GraphPad-Prism software.

FIG. 6 shows various graphs depicting the biologic activities of HL840 and structurally similar compounds. Specifically, FIG. 6 shows RAW 264.7 cells cultured in osteoclast (OC)-differentiating conditions in the presence or absence of various, and IC50 values.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating or ameliorating an immunoregulatory abnormality comprising administering to a patient in need thereof
   1) one or more anti-inflammatory and/or anti-rheumatic compositions; and
   2) a therapeutically effective amount of a pharmaceutical composition comprising a compound encompassed within Formulas I, II, III, and IV:

(Formula I)
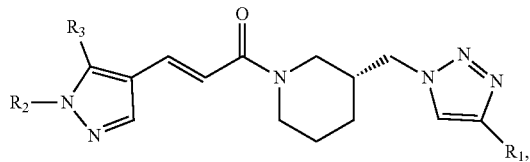

(Formula II)
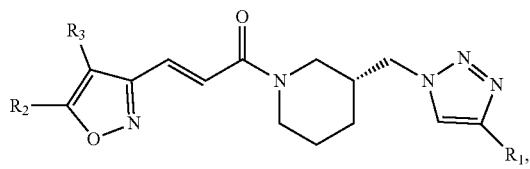

(Formula III)
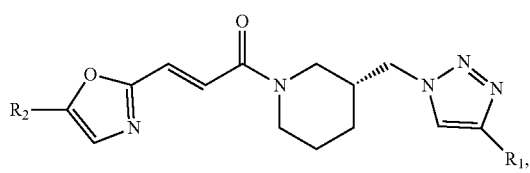

(Formula IV)
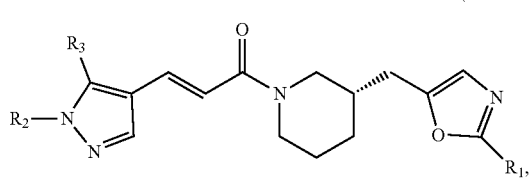

and pharmaceutically acceptable salts thereof;
wherein R₁ is selected from the group consisting of

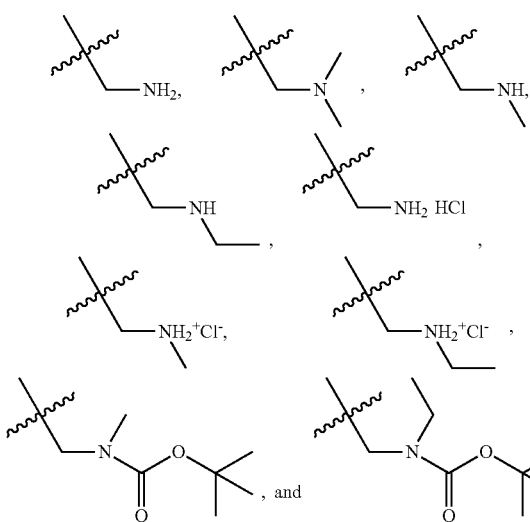

wherein R₂ is selected from the group consisting of CH₃,

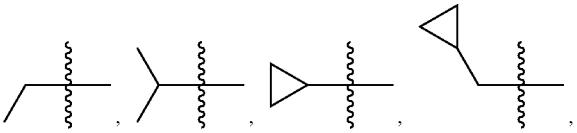

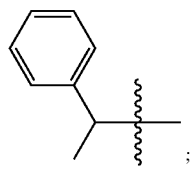

wherein R₃ is selected from the group consisting of hydrogen and fluorine, wherein the immunoregulatory abnormality is selected from the group consisting of Paget's disease of bone, chronic rheumatoid arthritis.

2. The method according to claim 1, wherein the pharmaceutical composition comprises a compound selected from the group consisting of:

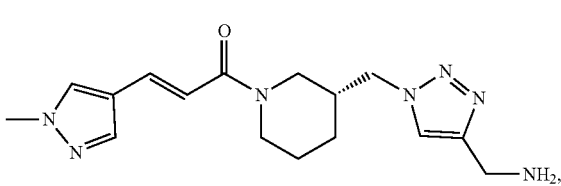

(R)-HL840

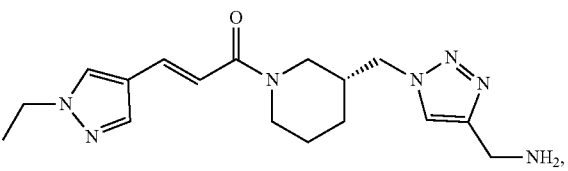

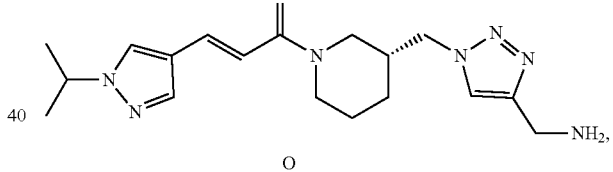

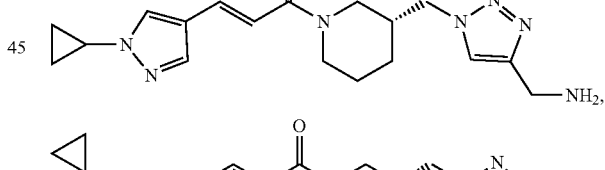

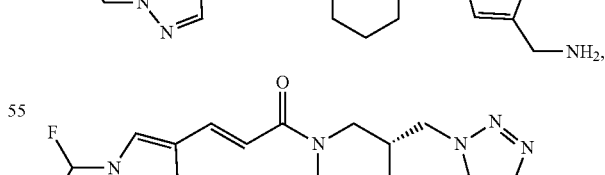

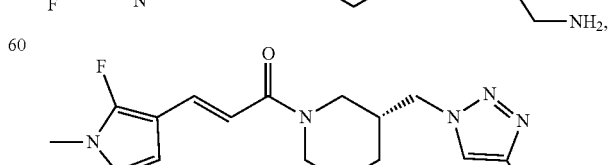

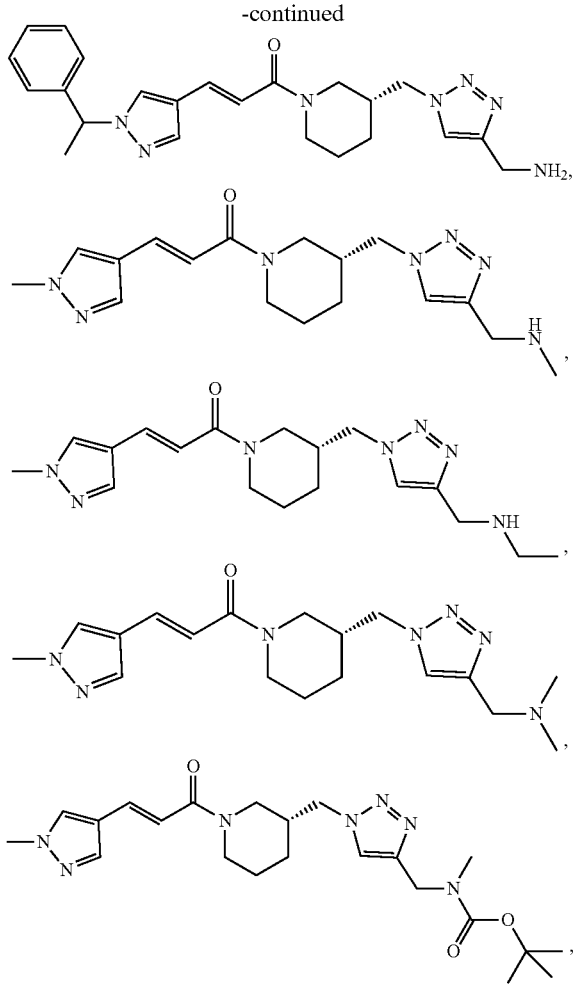
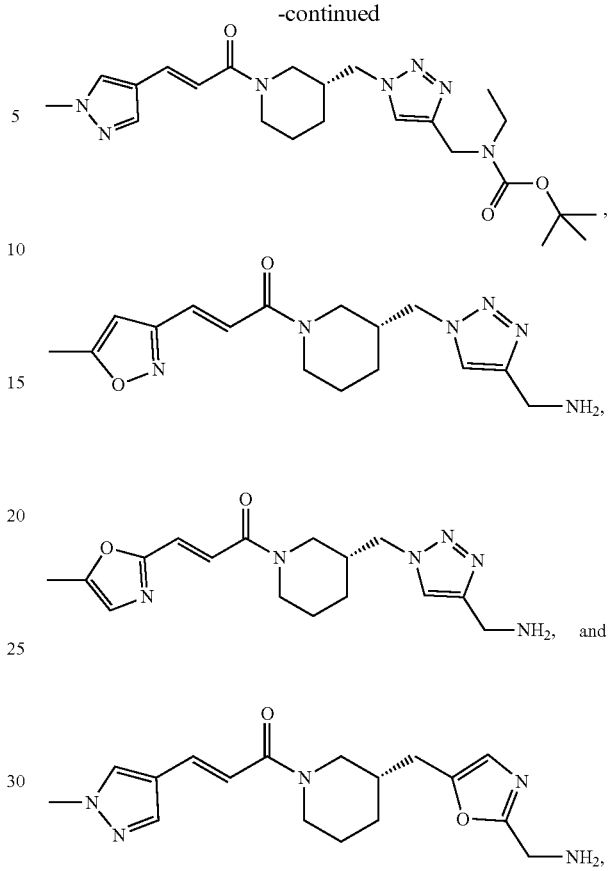
or a pharmaceutically acceptable salt thereof, and a pharmaceutically acceptable carrier.
* * * * *

UNITED STATES PATENT AND TRADEMARK OFFICE
CERTIFICATE OF CORRECTION

| | |
|---|---|
| PATENT NO. | : 11,168,071 B2 |
| APPLICATION NO. | : 16/896546 |
| DATED | : November 9, 2021 |
| INVENTOR(S) | : Joseph Holoshitz and Andrew White |

It is certified that error appears in the above-identified patent and that said Letters Patent is hereby corrected as shown below:

In the Specification

Please insert the following paragraph in Column 1, after the title:
--This invention was made with government support under AR059085 awarded by the National Institutes of Health. The government has certain rights in the invention.--

Signed and Sealed this
Fourth Day of June, 2024

Katherine Kelly Vidal
*Director of the United States Patent and Trademark Office*